(12) United States Patent
Dupont et al.

(10) Patent No.: US 11,712,329 B2
(45) Date of Patent: Aug. 1, 2023

(54) AIRWAY STENTS

(71) Applicant: Children's Medical Center Corporation, Boston, MA (US)

(72) Inventors: Pierre Dupont, Wellesley, MA (US); Aditya K. Kaza, Chestnut Hill, MA (US)

(73) Assignee: Children's Medical Center Corporation, Boston, MA (US)

( * ) Notice: Subject to any disclaimer, the term of this patent is extended or adjusted under 35 U.S.C. 154(b) by 260 days.

(21) Appl. No.: 16/838,625

(22) Filed: Apr. 2, 2020

(65) Prior Publication Data
US 2020/0315770 A1 Oct. 8, 2020

Related U.S. Application Data

(60) Provisional application No. 62/829,395, filed on Apr. 4, 2019.

(51) Int. Cl.
| | | |
|---|---|---|
| *A61F 2/04* | (2013.01) | |
| *A61B 1/267* | (2006.01) | |
| *A61F 2/962* | (2013.01) | |
| *A61F 2/88* | (2006.01) | |
| *A61F 2/95* | (2013.01) | |

(52) U.S. Cl.
CPC ............. *A61F 2/04* (2013.01); *A61B 1/267* (2013.01); *A61F 2/88* (2013.01); *A61F 2/962* (2013.01); *A61F 2002/043* (2013.01); *A61F 2002/046* (2013.01); *A61F 2002/9528* (2013.01); *A61F 2230/0091* (2013.01); *A61F 2250/0098* (2013.01)

(58) Field of Classification Search
CPC .......... A61B 1/267; A61B 2017/00349; A61F 2002/9528; A61F 2230/0091; A61F 2002/9511; A61F 2/88
See application file for complete search history.

(56) References Cited

U.S. PATENT DOCUMENTS 5,643,309 A * 7/1997 Myler .................. A61F 2/95
606/191
6,309,397 B1 * 10/2001 Julian .................. A61B 34/30
128/898

(Continued)

FOREIGN PATENT DOCUMENTS

| WO | WO-9422379 A1 * | 10/1994 | ............ A61F 2/88 |
| WO | WO-2008142677 A2 * | 11/2008 | .......... A61B 17/064 |
| WO | WO 2019/180291 | 9/2019 | |

OTHER PUBLICATIONS

Al-Ayoubi and Bhora, "Current readings: the role of stenting in tracheobronchial disease," Seminars in Thoracic and Cardiovascular Surgery, 2014, 26(1):71-75.

(Continued)

*Primary Examiner* — Brian E Pellegrino
(74) *Attorney, Agent, or Firm* — Fish & Richardson P.C.

(57) ABSTRACT

A stent assembly for insertion into an airway of a patient includes a stent defining an interior pathway along a length of the stent. The stent assembly includes a removal instrument for removal of the stent from the airway of the patient. The removal instrument is configured to cause a helical motion of the stent to remove the stent from the airway of the patient.

23 Claims, 32 Drawing Sheets
(24 of 32 Drawing Sheet(s) Filed in Color)

(56) References Cited

U.S. PATENT DOCUMENTS

| | | | | |
|---|---|---|---|---|
| 2002/0188344 | A1* | 12/2002 | Bolea | A61F 2/95 623/1.11 |
| 2011/0054591 | A1* | 3/2011 | Sahatjian | A61F 2/88 623/1.42 |
| 2017/0245977 | A1* | 8/2017 | Foster | A61F 2/88 |

OTHER PUBLICATIONS

American Association for Respiratory Care, "AARC Clinical Practice Guidelines. Endotracheal suctioning of mechanically ventilated patients with artificial airways," Respiratory Care, 2010, 55(6):758-764.
Antón-Pacheco et al., "Initial experience with a new biodegradable airway stent in children: is this the stent, we were waiting for?" Pediatric Pulmonology, 2016, 51(6):607-612.
Beamis et al., "ERS/ATS statement on interventional pulmonology." The European Respiratory Journal, 2002, 19(2):356-373.
Bolliger et al., "Silicone stents in the management of inoperable tracheobronchial stenoses. Indications and limitations," Chest Journal, 1993, 104(6):1653-1659.
Chao et al., "Biodegradable cisplatin-eluting tracheal stent for malignant airway obstruction: in vivo and in vitro studies." Chest, 2013, 144(1):193-199.
Clifton-Koeppel, "Endotracheal tube suctioning in the newborn: a review of the literature," Newborn and Infant Nursing Reviews, 2006, 6(2):94-99.
Cooper et al., "Use of silicone stents in the management of airway problems." The Annals of Thoracic Surgery, 1989, 47(3):371-378.
Dumon, "A dedicated tracheobronchial stent." Chest Journal, 1990, 97(2):328-332.
Dutau, et al., "Biodegradable airway stents-bench to bedside: a comprehensive review." Respiration, 2015, 90(6):512-521.
FDA, "Public Health Notification: Complications from Metallic Tracheal Stents in Patients with Benign Airway Disorders," Jul. 29, 2005, retrieved from URL <http://www.fda.gov/MedicalDevices/Safety/AlertsandNotices/PublicHealthNotifications/ucm062115.html>.
Folch and Keyes, "Airway stents." Annals of Cardiothoracic Surgery, 2018. 7(2):273-283.
Kumar el al., "Airway obstruction and ventilator dependency in young children with congenital cardiac defects: a role for self-expanding metal stents," Intensive Care Medicine, 2002, 28(2):190-195.
Lee and Mehta, "Airway Stents." Clinics in Chest Medicine. 2.010. 31(1) 141-150.
Lischke et al., "Novel biodegradable stents in the treatment of bronchial stenosis after lung transplantation," European Journal of Cardiothoracic Surgery, 2011, 40(3):619-624.
Lunn et al., "Endoscopic removal of metallic airway stents," Chest, 2005, 127(6):2106-2112.
Mochizuki et al., "Endoscopic submucosal dissection combined with the placement of biodegradable stents for recurrent esophageal cancer after chemoradiotherapy," Journal of Gastrointestinal Cancer, 2012, 43(2):324-328.
Morrison et al., "Mitigation of tracheobronchomalacia with 3d-printed personalized medical devices in pediatric patients," Science Translational Medicine, 2015, 7(285):285ra64-285ra64.
Noppen et al., "A New Screw-Thread Tracheal Endoprosthesis," J. Bronchol., 1996, 3(1):22-26.
Novotny et al., "Novel biodegradable polydioxanone stents in a rabbit airway model." J. Thorac. Cardiovasc. Surg., 2012, 143(2):437-444.
Saito et al., "New tubular bioabsofbable knitted airway stent: biocompatibility and mechanical strength." J. Thorac. Cardiovasc. Surg., 2002, 123(1):161-167.
Serio et al., "Tracheobronchial obstruction: follow-up study of 100 children treated with airway stenting." European Journal of Cardio-Thoracic Surgery, 2014, 45(4):e100-e109.
Sztano and Rovo, "Response to the letter to the Editor Biodegradable airway stents in infants—Potential life-threatening pitfalls, ." International Journal of Pediatric Otorhinolaryngology, 2017, 98:175-176.
Sztano et al., "Biodegradable airway stents in infants—potential life-threatening pitfalls." International Journal of Pediatric Otorhinolaryngology, 2016, 91:86-89.
Vondrys et al., "First experience with biodegradable airway stents in children," The Annals of Thoracic Surgery; 2011, 92(5):1870-1874.
Vondrys et al., Letter to the Editor regarding "Biodegradable airway stents in infants—Potential life-threatening pitfalls." International Journal of Pediatric Otorhinolaryngology, 2017, 98:174.
Zhu et al., "The current status of biodegradable stent to treat benign luminal disease," Materials Today, 2017, 20(9):516-529.
Zopf et al., "Bioresorbable airway splint created with a three-dimensional printer," New England Journal of Medicine, 2013, 368(21):2043-2045.

\* cited by examiner

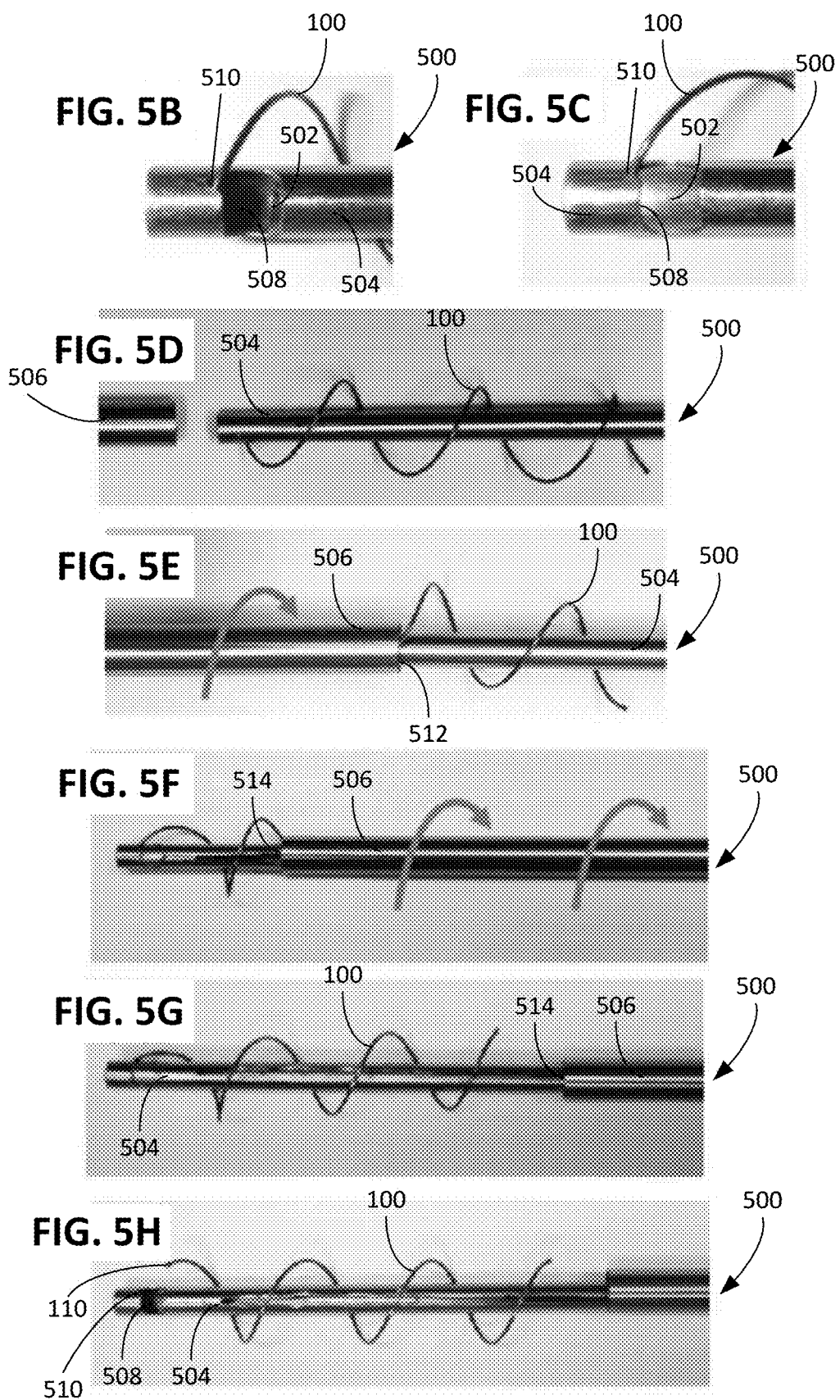

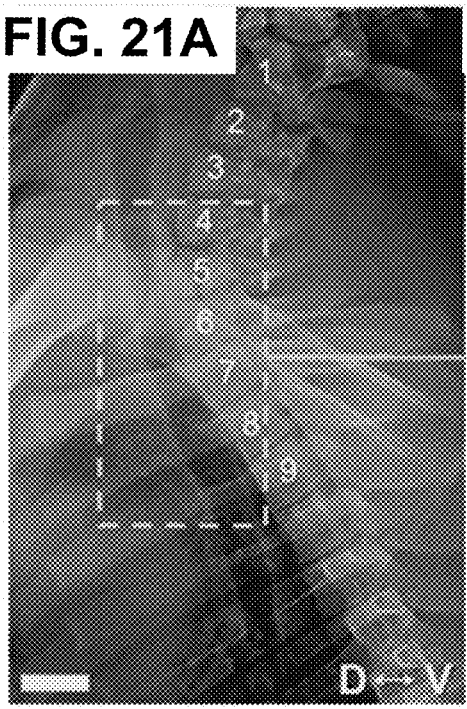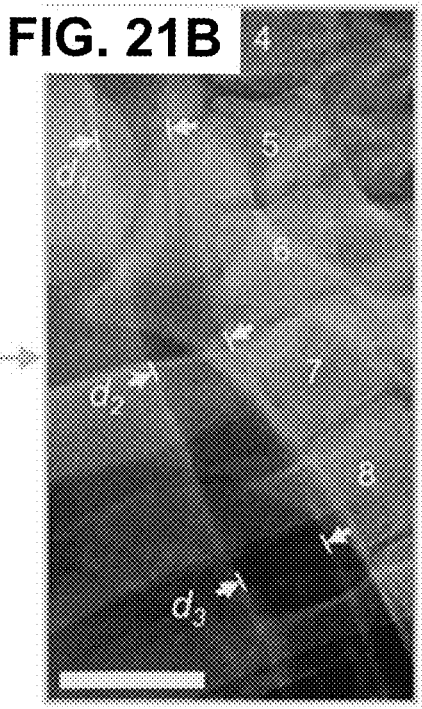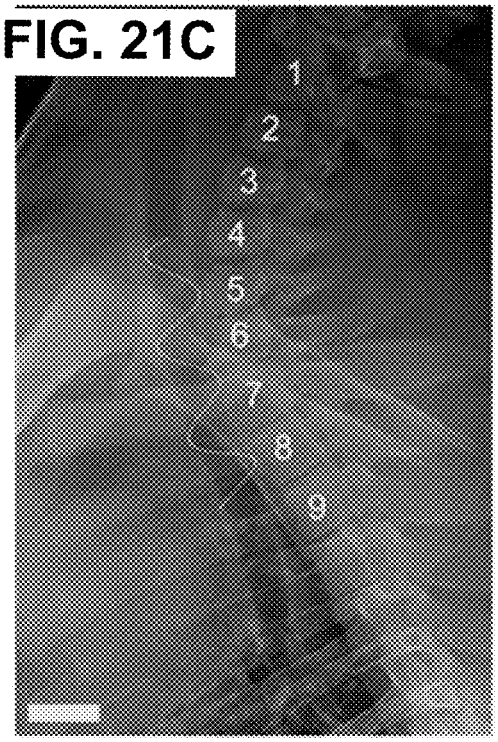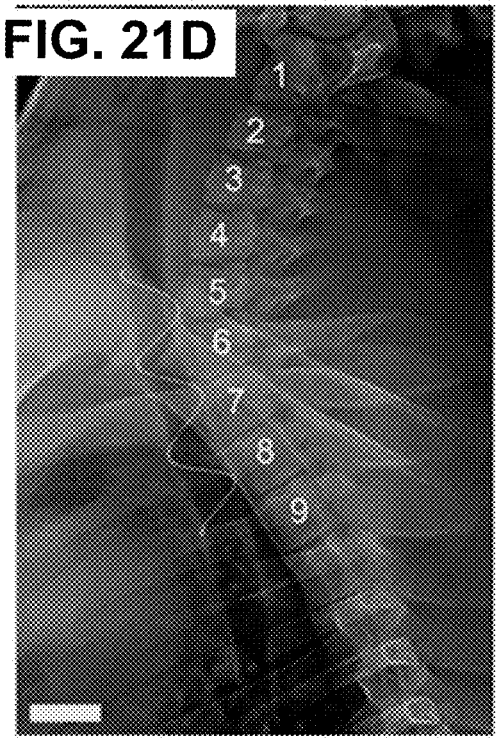

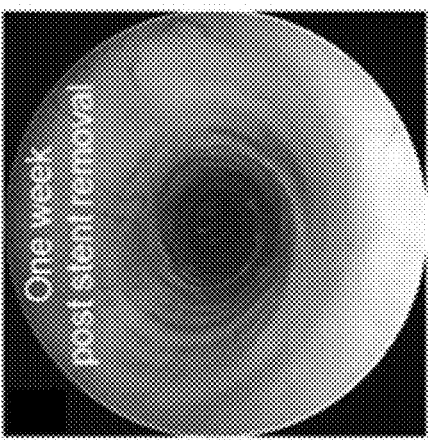
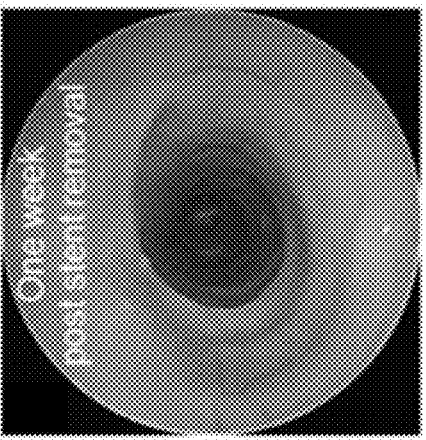
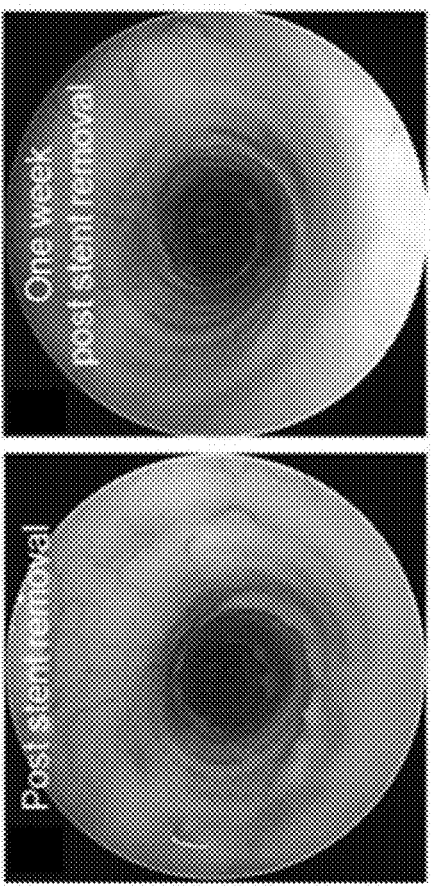
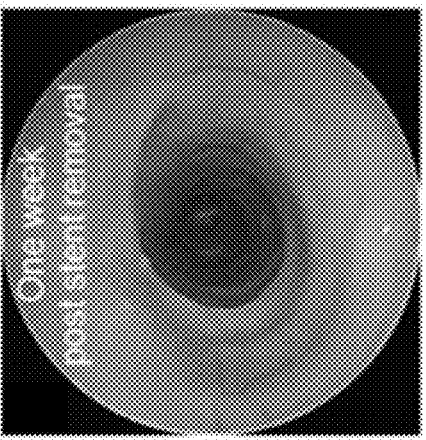
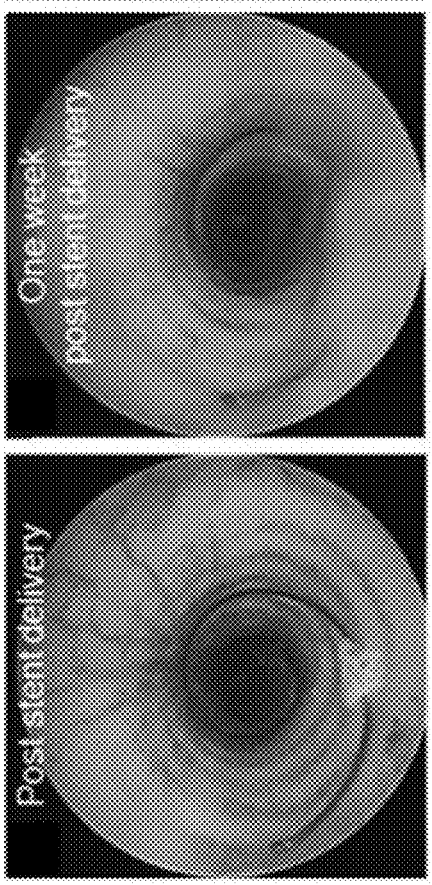
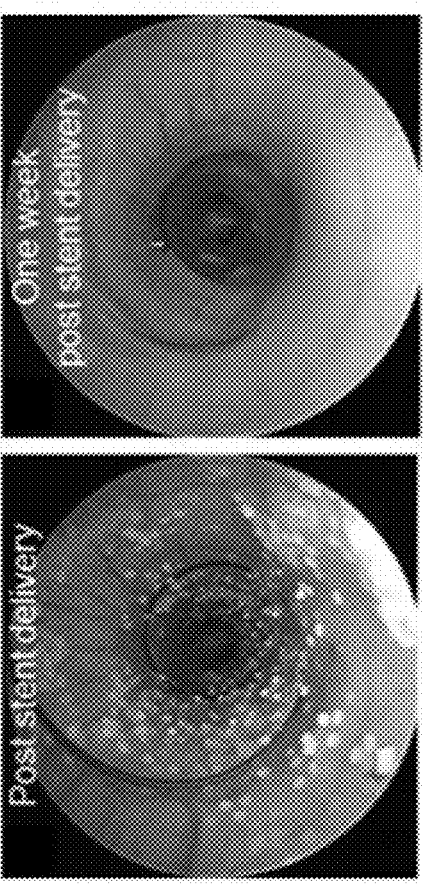
FIG. 22A  FIG. 22B  FIG. 22C  FIG. 22D
FIG. 22E  FIG. 22F  FIG. 22G  FIG. 22H

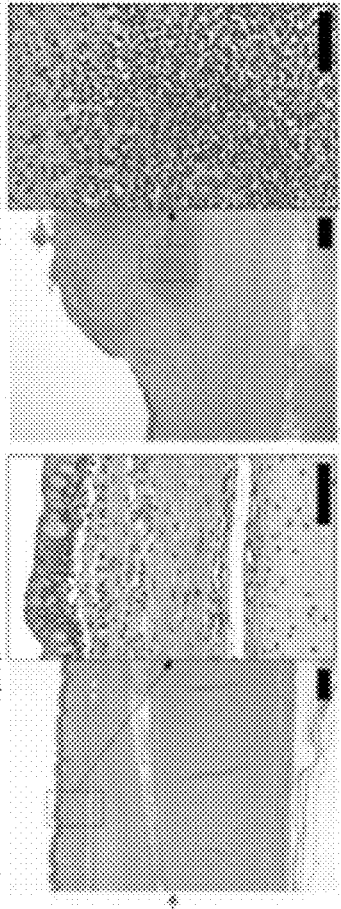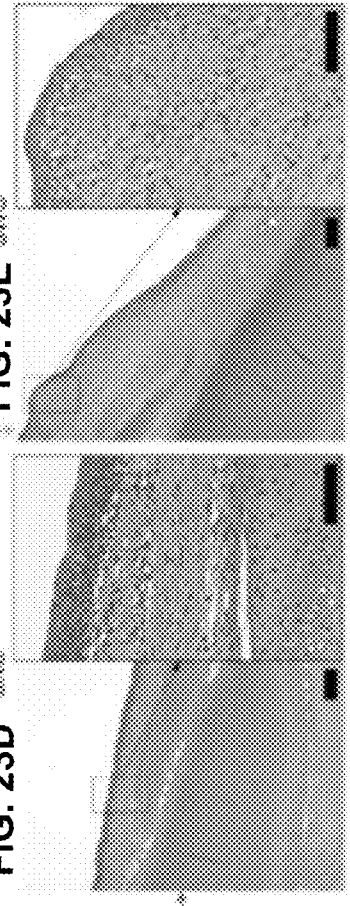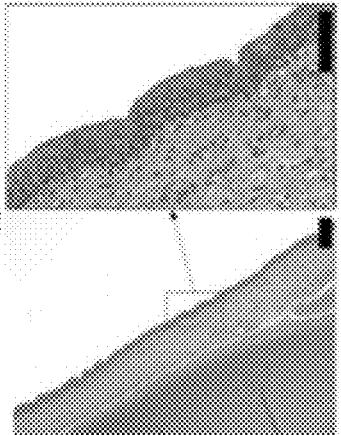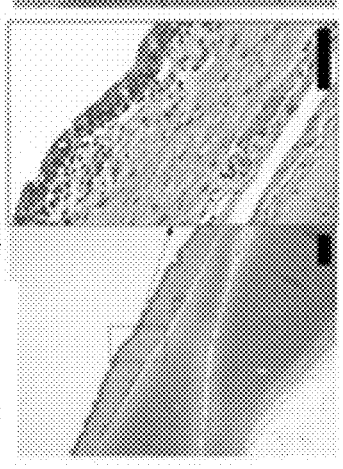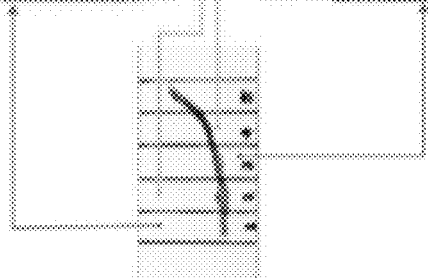
FIG. 23A  FIG. 23B  FIG. 23C  FIG. 23D  FIG. 23E  FIG. 23F  FIG. 23G

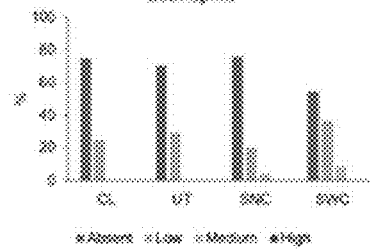
FIG. 24A Eosinophils
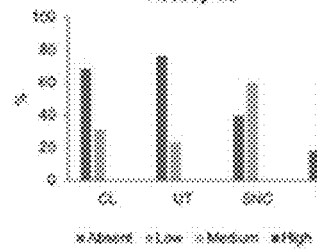
FIG. 24B Neutrophils
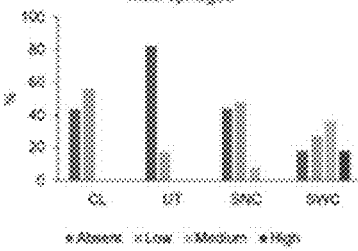
FIG. 24C Macrophages
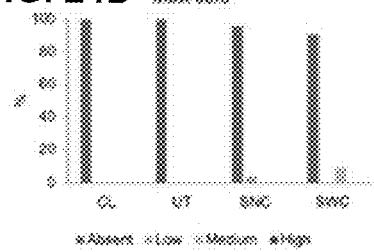
FIG. 24D Mast cells
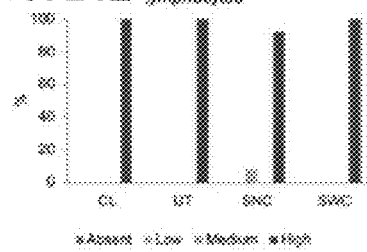
FIG. 24E Lymphocytes
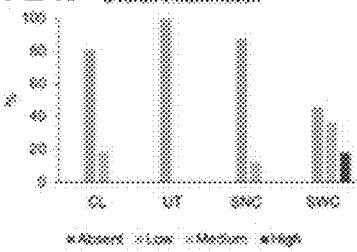
FIG. 24F Overall inflammation
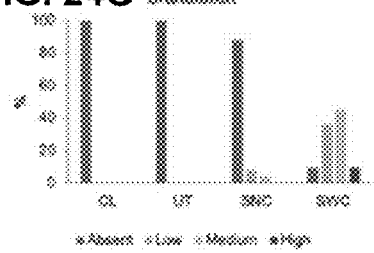
FIG. 24G Granulation
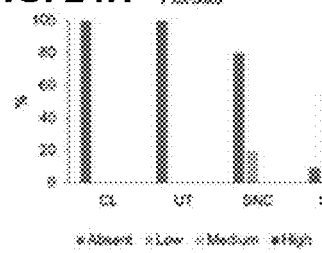
FIG. 24H Fibrosis
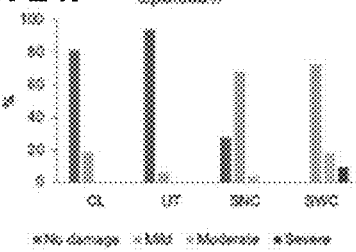
FIG. 24I Epithelium
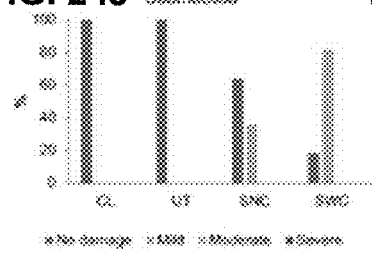
FIG. 24J Submucosa
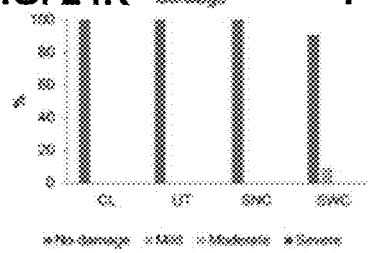
FIG. 24K Cartilage
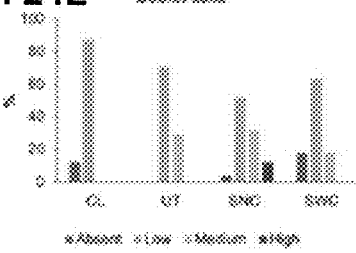
FIG. 24L Goblet cells

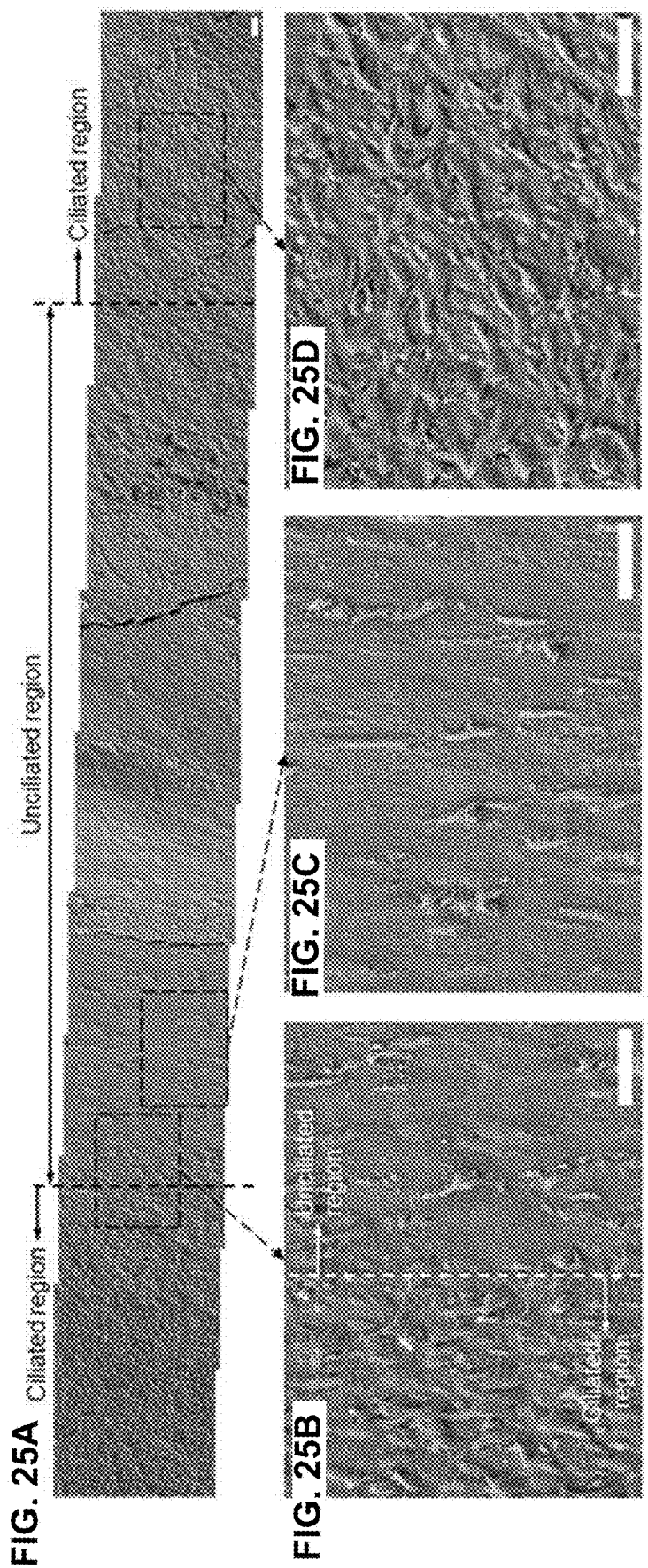

AIRWAY STENTS

CLAIM OF PRIORITY

This application claims priority U.S. Provisional Patent Application Ser. No. 62/829,395, filed on Apr. 4, 2019, the entire contents of which are hereby incorporated by reference.

STATEMENT OF GOVERNMENT RIGHTS

This invention was made with government support under Grant no. HL089136, awarded by The National Institutes of Health. The government has certain rights in the invention

TECHNICAL FIELD

This specification relates to stents, in particular, for airways.

BACKGROUND

Tracheobronchomalacia is a congenital defect of the central airways and has been identified in up to 15% of infants and 30% of young children undergoing bronchoscopic examination for respiratory distress. The condition can arise due to intrinsic weakness of the wall and cartilaginous support. For these children, during dynamic expiration and coughing at low lung volume, pleural pressure exceeds intraluminal pressure resulting in airway collapse. One way to treat tracheobronchomalacia is to apply positive pressure ventilation of 5-20 cm H2O to raise the intraluminal pressure sufficiently to prevent collapse during expiration. During the 3- to 9-month treatment period, a child remains connected to a ventilator and is closely monitored to provide regular suctioning of the endotracheal tube. Even with suctioning, the inability to clear mucus leads to an increased risk of airway infections including pneumonia and tracheitis. Adults also suffer from tracheabronchomalacia and excessive dynamic airway collapse and so could benefit from improved airway stents.

SUMMARY

A stent can be used to treat certain respiratory conditions. The stent can be placed in an airway of a patient to provide structural support to the airway, thereby helping to prevent collapse of the airway that could result from tracheobronchomalacia and other respiratory conditions. The stent can include a helically arranged structure that fits in the airway of the patient and engages tissue defining the airway of the patient. In some implementations, a stent can be formed while disposed in the airway of the patient.

Advantages of the foregoing and other implementations described herein may include, but are not limited to, those described below and herein elsewhere. The stents can provide support to airways of patients. This support can be equivalent to support provided by positive pressure ventilation methods. Use of the stents can reduce the need for sustained use of ventilators for patients that suffer from airway conditions such as tracheobronchomalacia.

The stents described herein can also provide one or more of the following advantages over other stents for patient airways. Compared to stents made of metal meshes, the stents described herein can have a lower risk of inducing growth of granulation tissue when placed into airways. The helically arranged structure of the stents can be less likely to impede cilia-mediated mucus streaming. In some examples of the stents described herein, a stent, when placed into an airway, can be less prone migrating relative to the airway of the patient. The stent can be easily removed without causing an excessive amount of trauma to the patient. The stent can have a relatively compact design compared to conventional stents, thus reducing the amount of foreign material that is placed into an airway to treat a condition of the airway. The stent can be used on neonates, infants, and other individuals with confined airways that cannot tolerate highly invasive procedures.

The delivery, removal, and grasping instruments described herein can provide one or more of the following advantages. The instruments can improve the ease with which operators can perform stent procedures for treating respiratory conditions. For example, a delivery instrument can easily engage with a stent such that an operator can easily manipulate the stent and position the stent accurately within an airway of a patient. The delivery instrument can enable atraumatic placement of the stent, thus minimizing the intrusiveness to the patient. An operator can easily use a removal instrument to remove the stent from the airway of the patient without a high risk of causing trauma to the patient's airway. The grasping instrument can enable the operator to regrasp a stent in the event that the removal instrument loses engagement with the stent. The grasping instrument can thus provide another tool for an operator to use to manipulate the stent in an easy way.

The stents and methods described herein can also be used to create custom-fit stents that account for the variability in airway anatomy associated with tracheobronchomalacia and the impact of adjacent cardiovascular structures. Compared to approaches in which a mold is 3D printed or other created outside of the body, the methods described herein use the patient's airway as the mold to reduce the cost and/or time involved in stent customization. The technology can account for variability and impingement of adjacent cardiovascular structures that could be otherwise difficult to accommodate using standard-fit stents.

In one aspect, a stent for use in an airway of a patient is featured. The stent includes a helically arranged structure defining an interior pathway along a length of the stent, a distal protruding element disposed at a distal end of the helically arranged structure, and a proximal protruding element disposed at a proximal end of the helically arranged structure. The helically arranged structure is sized to fit in the airway of the patient.

In another aspect, a stent assembly for insertion into an airway of a patient is featured. The stent assembly includes a stent including a helically arranged structure defining an interior pathway along a length of the stent, and a delivery instrument for delivery of the stent into the airway of the patient.

In another aspect, a method for delivering a stent into an airway of a patient is featured. The method includes inserting a delivery instrument into the airway of the patient, withdrawing an outer cannula of the delivery instrument from the airway of the patient; and retracting an inner cannula of the delivery instrument to release the stent from the delivery instrument. The inner cannula is concentric with the outer cannula. The stent is disposed between the inner cannula and the outer cannula.

In another aspect, a method for removing a stent from an airway of a patient is featured. The method includes inserting a removal instrument into the airway of the patient, engaging the removal instrument with the stent, and rotating a portion of the removal instrument to cause retraction of the stent into the cannula.

In another aspect, a method for forming a stent for an airway of a patient is featured. The method includes inserting a stent assembly into the airway of the patient, expanding an expandable catheter of the stent assembly, irradiating a stent of the stent assembly with light from a light guide of the stent assembly, and removing the expandable catheter and light guide from the airway of the patient. The expandable catheter is disposed in an interior pathway defined by the stent, and the light guide is disposed in the interior pathway.

In another aspect, a stent for use in an airway of a patient is featured. The stent includes a helically arranged structure defining an interior pathway along a length of the stent. The helically arranged structure is sized to fit in the airway of the patient.

In another aspect, a stent assembly for insertion into an airway of a patient is featured. The stent assembly includes a stent including a curable material, and a delivery instrument for delivery of the stent into the airway of the patient.

In another aspect, a stent assembly for insertion into an airway of a patient includes a stent including a helically arranged structure defining an interior pathway along a length of the stent. The stent assembly includes a removal instrument for removal of the stent from the airway of the patient. The removal instrument is configured to cause a helical motion of the stent to remove the stent from the airway of the patient.

In some implementations, the removal instrument can include an inner cannula and an outer cannula. An inner cannula of the removal instrument can be concentric with an outer cannula of the removal instrument. The removal instrument can include a grasping device. The grasping device can be connected to one of the concentric cannulas of the removal instrument by a helical joint.

In some implementations, the removal instrument can include an imaging device.

In some implementations, the stent assembly can further include a delivery instrument for delivery of the stent into the airway of the patient. The stent can include a curable material.

In some implementations, the curable material can be within a shell of the stent.

In some implementations, the shell can include end portions including metal.

In some implementations, the helically arranged structure can include a continuous, helically shaped wire. In some implementations, a relationship between a pitch of the helically shaped wire and a diameter of the wire can be selected such that when the stent is inserted in the airway of the patient, the stent provides radial support to the airway equivalent to a target positive pressure ventilation of the airway.

In some implementations, the helically arranged structure can include an elongated spine oriented along the length of the stent, and helically arranged arches attached to the spine.

In some implementations, a helix angle of the helically arranged structure can be between 15° and 35°.

In some implementations, the helically arranged structure can be configured to provide an outward pressure equivalent to up to about 20 cm H2O.

In some implementations, an expandable catheter can be disposed in the interior pathway defined by the helically arranged structure. In some implementations, a lumen can be defined through the expandable catheter.

In some implementations, a light guide can be disposed in the interior pathway defined by the helically arranged structure of the stent.

In some implementations, the helically arranged structure can include a curable material.

In some implementations, the helically arranged structure can include a hollow tube filled with the light-curable material.

In some implementations, the helically arranged structure can include a continuous, helically shaped wire.

In some implementations, the helically arranged structure can include an elongated spine oriented along the length of the stent, and helically arranged arches attached to the spine.

In some implementations, the stent can be disposed in an interior of a cannula of the delivery instrument for delivery into the airway of the patient.

In some implementations, the delivery instrument can include multiple concentric cannulas.

In some implementations, for delivery of the stent into the airway of the patient, a protruding element on a distal end of the stent can be held between adjacent cannulas of the multiple concentric cannulas.

In some implementations, the stent assembly includes a removal instrument for removal of the stent from the airway of the patient.

In some implementations, the removal instrument can include multiple concentric cannulas. In some implementations, the removal instrument can include a grasping device configured to grasp a proximal end of the stent for removal of the stent from the airway of the patient. In some implementations, the grasping device can include forceps. In some implementations, the grasping device can be connected to a cannula of the removal instrument by a helical joint. In some implementations, a pitch of the helical joint can match the pitch of the helically arranged structure of the stent. In some implementations, the removal instrument can include an imaging device.

In some implementations, the portion of the removal instrument can include a helical joint, and the stent can include a helically arranged structure. A pitch of the helical joint can match a pitch of the helically arranged structure of the stent.

In some implementations, withdrawing the outer cannula can include unscrewing the outer cannula from the inner cannula.

In some implementations, the method can include disposing the stent in the delivery instrument. In some implementations, disposing the stent in the delivery instrument can include holding a protruding element on a distal end of the stent between the inner cannula and an adjacent cannula of the delivery instrument. In some implementations, retracting the inner cannula can include releasing the protruding element from the delivery instrument. In some implementations, disposing the stent in the delivery instrument can include screwing the stent into the outer cannula.

In some implementations, the stent can include a light-curable material. Irradiating the helically arranged structure can include curing the light-curable material of the structure. Irradiating the stent can include curing the helically arranged structure in the shape of the airway of the patient.

In some implementations, expanding the expandable catheter can include expanding the expandable catheter such that a cross-section of the expandable catheter matches a cross-section of the airway.

In some implementations, the method can include deflating the expandable catheter.

In some implementations, inserting the stent assembly can include inserting the stent assembly via a guidewire.

In some implementations, the stent can include a helically arranged structure defining the interior pathway along the length of the stent.

In some implementations, the curable material can include at least one of a light-curable material, a heat-curable material, or a first material and a second material that are curable when mixed.

In some implementations, the stent can include a helically arranged structure defining an interior pathway along a length of the stent, the helically arranged structure being sized to fit in the airway of the patient.

In some implementations, the stent can include a mesh or woven structure defining an interior pathway along a length of the stent, the helically arranged structure being sized to fit in the airway of the patient.

In some implementations, the curable material is within a shell of the stent.

In some implementations, the shell includes end portions including metal.

In some implementations, a shell of the stent is formed from a polymer.

In some implementations, irradiating the stent includes positioning the light guide at multiple locations relative to the stent and emitting light through the light guide at each of the multiple locations.

In some implementations, at least a portion of the shell can include a radiopaque material.

In some implementations, a distal end or a proximal end of the shell can include the radiopaque material.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 5B-5H illustrate a stent and a delivery instrument manipulating the stent.

FIGS. 21A-21D illustrate x-ray images used for tracheal size estimation and stent migration in swine trachea.

FIGS. 22A-22H illustrate endoscopic images of trachea of a swine.

FIGS. 23A-23G illustrate stained lateral tracheal sections from experimental and control animals.

FIGS. 24A-24L illustrate histological evaluations of tissues collected from experimental and control animals.

FIGS. 25A-25D illustrate scanning electron microscope (SEM) images of cilitated and unciliated regions of animal tissue.

Like reference numbers and designations in the various drawings indicate like elements.

DETAILED DESCRIPTION

A physical stent can be inserted into an airway to prevent airway collapse. Airway stents can be made of a variety of materials and can have a variety of configurations. For example, metal mesh vascular stents can be used to treat tracheobronchomalacia. These stents can cause potential issues. First, granulation tissue can grow in response to the presence of a foreign body. Second, the lining of the trachea can naturally grow through and cover a mesh stent making it difficult to remove the stent from the patient's airway. Third, metal stents have the potential to wear through the surrounding tissue. Other approaches for addressing airway collapse include inserting solid silicone tubes into an airway. These tubes have large thicknesses and, for adult populations, can reduce airway diameter. In addition, these tubes can have a high migration rate, and can block mucociliary function over a length of the stent resulting in mucous plugging and inspissated secretions that impede gas exchange.

As described herein, stents with helically arranged structures can avoid at least some of these drawbacks associated with metal mesh stents and silicone tubes. The helical shape can act like a screw inside the airway resisting migration. It also does not impede mucus flow. Furthermore, by using a helical motion to remove it from the airway, it can be removed with minimal trauma even if the epithelium has grown over it. Also, the helical shape can reduce the amount of foreign material introduced in the airway of a patient and can potentially reduce granulation tissue.

Example Stents

Figure 1:
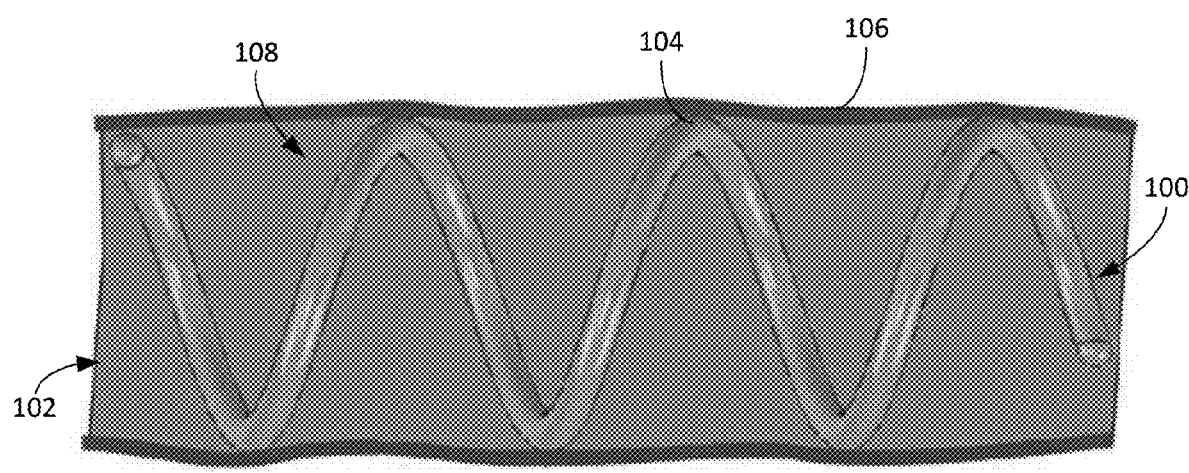
FIG. 1 is a schematic view of a stent in an airway of a patient.

FIG. 1 schematically illustrates a stent 100 inserted into an airway 102 of a patient. The stent 100 includes a helically arranged structure 104 configured to engage with tissue 106 defining the airway 102 and sized to fit within the airway 102 of the patient. The helically arranged structure 104 defines an interior pathway 108 along a length of the stent 100. The interior pathway 108 extends longitudinally along an entire length of the stent 100. This interior pathway 108 allows fluid, e.g., air, to travel through the length of the stent 100 and thus allows the stent 100 to be used in the airway 102 of the patient. In addition, the interior pathway 108 allows, as described herein, delivery, removal, or regrasping instruments to advance through the stent 100 such that these instruments can manipulate a distal end of the stent 100.

Figure 2:
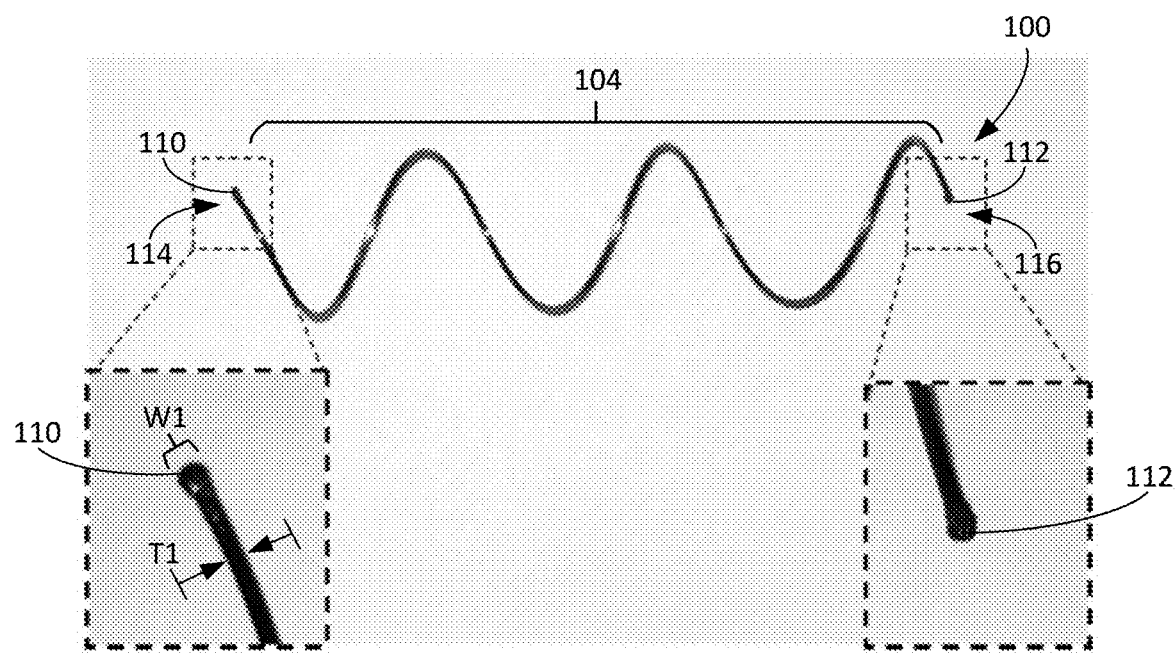
FIG. 2 is a side view of an example of a stent.

Referring to FIG. 2, the stent 100 includes protruding elements 110, 112 on distal and proximal ends 114, 116 of the helically arranged structure 104. The protruding elements 110, 112 have widths that are larger than a thickness T1 of the helically arranged structure 104. As described herein, these widths of the protruding elements 110, 112 allow the protruding elements 110, 112 to be easily held by delivery, removal, and regrasping instruments as described herein. In some implementations, the protruding elements 110, 112 can be blunt or rounded or have some other geometry that allows a greater area across which pressure is distributed when the protruding elements 110, 112 contact a surface, e.g., contact patient tissue. This can reduce the localized pressure on the tissue and thus reduce the likelihood that the stent 100 punctures tissue.

The protruding elements 110, 112 can have sizes and shapes that vary in implementations. For example, as shown in FIG. 2, the protruding elements 110, 112 are distal and proximal balls disposed on the distal and proximal ends 114, 116 of the helically arranged structure 104. In some implementations, the protruding elements 110, 112 can be rounded or prismatic, or have other shapes protruding from the helically arranged structure 104. In some implementations, the protruding elements 110, 112 are spherical or semispherical.

Figure 3A:
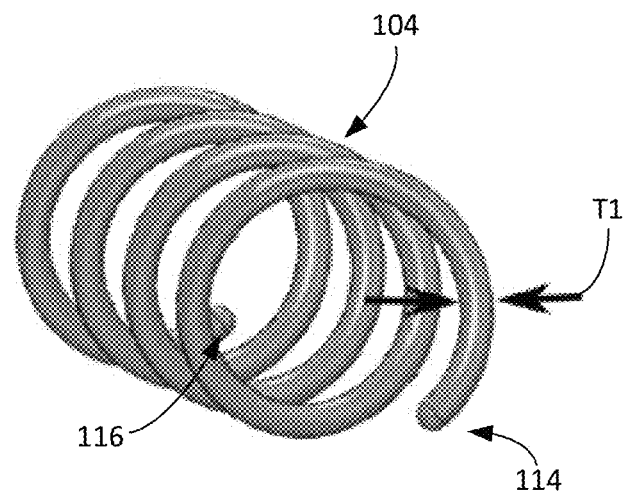
FIG. 3A is a perspective view of a helically arranged structure of the stent of FIG. 2A.

The protruding elements 110, 112 can have a width W1 that is at least 10%, 20%, 30%, or greater than a thickness T1 of the helically arranged structure 104. Referring also to FIG. 3A, which shows the helically arranged structure 104 of the stent 100, the helically arranged structure 104 can include a wire formed into a helical shape. For example, the wire can be a continuous, helically shaped wire extending from the distal end 114 to the proximal end 116 of the helically arranged structure 104. The thickness T1 of the helically arranged structure 104 can correspond to a diameter of the wire. In some implementations, the thickness T1 is between 0.1 mm and 1 mm, e.g., between 0.2 and 0.7 mm, between 0.3 and 0.6 mm, about 0.38 mm, or about 0.51 mm.

Figure 3B:
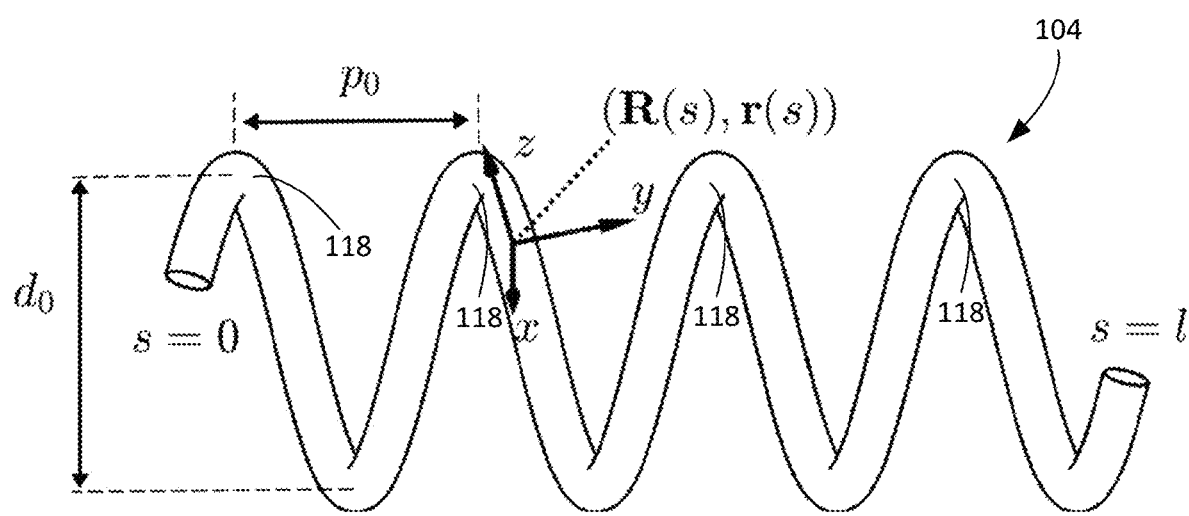
FIG. 3B is a diagram of the helically arranged structure of FIG. 3A.

FIG. 3B shows the helically arranged structure 104 of the stent 100 and certain dimensions characterizing the helically arranged structure 104. A center of the wire of the helically arranged structure 104 can extend along a helix. The helix, for example, is a helical path corresponding to a center line of the wire. A pitch $p_0$ of the helix corresponds to a distance between adjacent windings 118 of the helically arranged structure 104. A helix diameter $d_0$ of the helix can correspond to an outer diameter of the helix. An overall diameter of the helically arranged structure 104 can thus be the sum of the diameter of the helix and the thickness T1 of the helically arranged structure 104, e.g., a thickness of the wire defining the helically arranged structure 104. A helical angle of the helix can be between 15 and 35 degrees, e.g., between 15 and 25 degrees, 20 and 30 degrees, or 25 and 35 degrees. The overall diameter of the helically arranged structure 104 can be sized to be larger than the airway of the patient, e.g., by at least 1 mm, at least 3 mm, at least 5 mm, or more larger in diameter than the airway of the patient. Such a diameter allows the helically arranged structure to be elastically preloaded against the tissue defining the airway.

The helically arranged structure 104 can be designed with a specific relationship between the pitch $p_0$ and the helix diameter $d_0$, and hence a specific relationship between the pitch of the helically shaped wire and the overall diameter of the helically arranged structure 104. This relationship can be selected such that, when the stent 100 is inserted into the airway 102 of the patient (as shown in FIG. 1), the stent 100 can provide sufficient radial support to prevent the airway 102 from collapsing. The relationship can alternatively or additionally be selected to provide radial support equivalent to radial support provided by a target positive pressure ventilation of the airway 102 that would be sufficient to prevent the airway 102 from collapsing. For example, a target positive pressure ventilation of the airway 102 could be between 5 and 20 cm $H_2O$. The stent 100, and in particular, the helically arranged structure 104 of the stent 100 could be designed to produce an equivalent amount of pressure on the airway 102 when the stent 100 is inserted into the airway 102. In some implementations, the helically arranged structure 104 is configured to provide an outward pressure equivalent to up to about 10 cm $H_2O$, e.g., about 9 to 11 cm $H_2O$.

Example Delivery, Removal, and Grasping Methods and Instruments

The stent 100 is an example of a stent that can be placed into and removed from an airway, e.g., the airway 102, of a patient using instruments described herein. Specific methods of using a stent can vary in implementations, as can the instruments used to manipulate the stent for delivery into an airway, for removal from the airway, or for repositioning the stent.

Figure 4A:
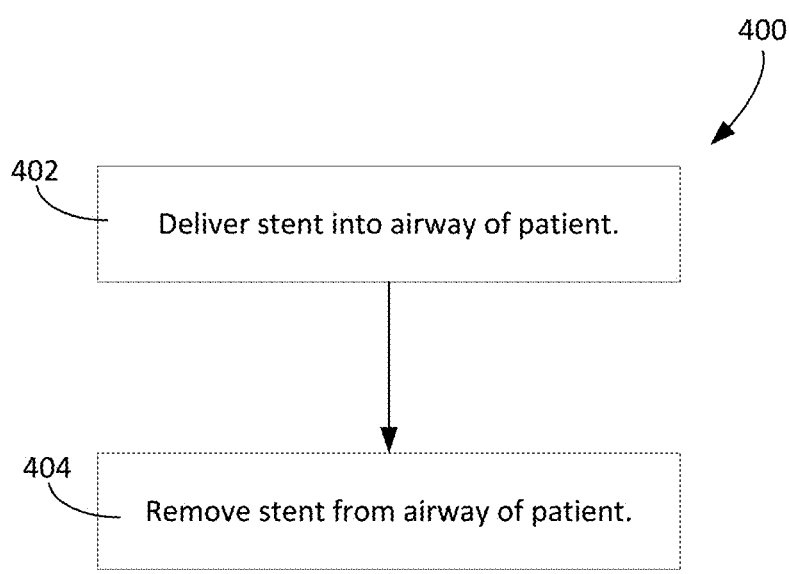
FIG. 4A is a flowchart of a method of using a stent in an airway of a patient.

FIG. 4A illustrates a method 400 of using a stent, e.g., the stent 100, in an airway, e.g., the airway 102, of a patient. In the method 400, a stent is delivered (402) into an airway of a patient. For treatment of a patient, the stent can remain in the airway for a treatment period over several days, weeks or months. In some cases, a stent is removed (404) from the airway after a certain period of time, e.g., after the treatment period has elapsed.

Figure 4B:
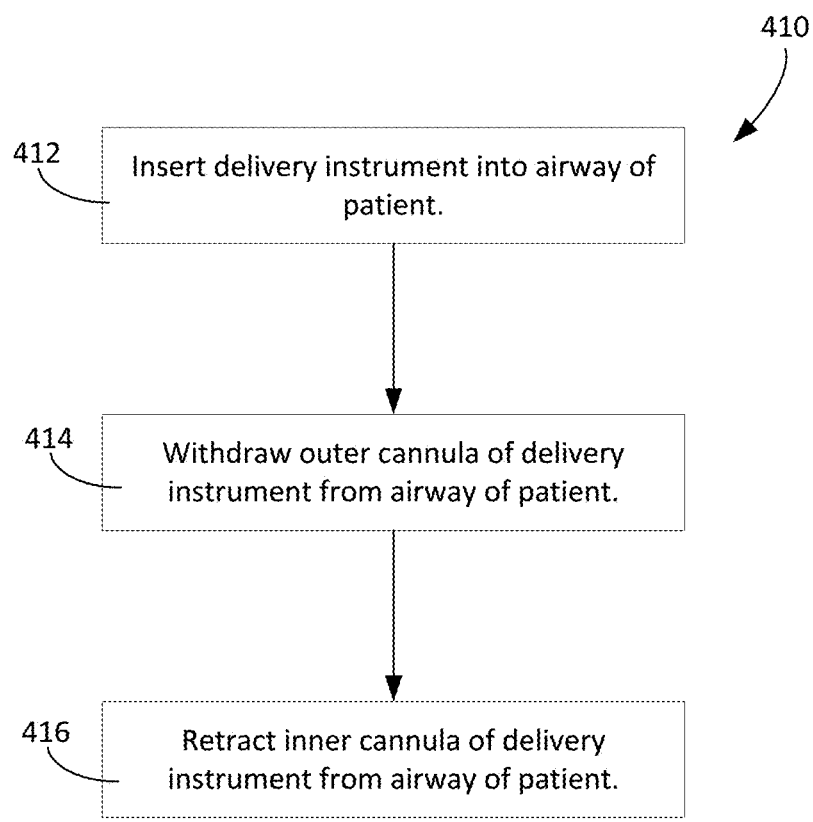
FIG. 4B is a flowchart of a method of delivering a stent to an airway of a patient.
Figure 5A:
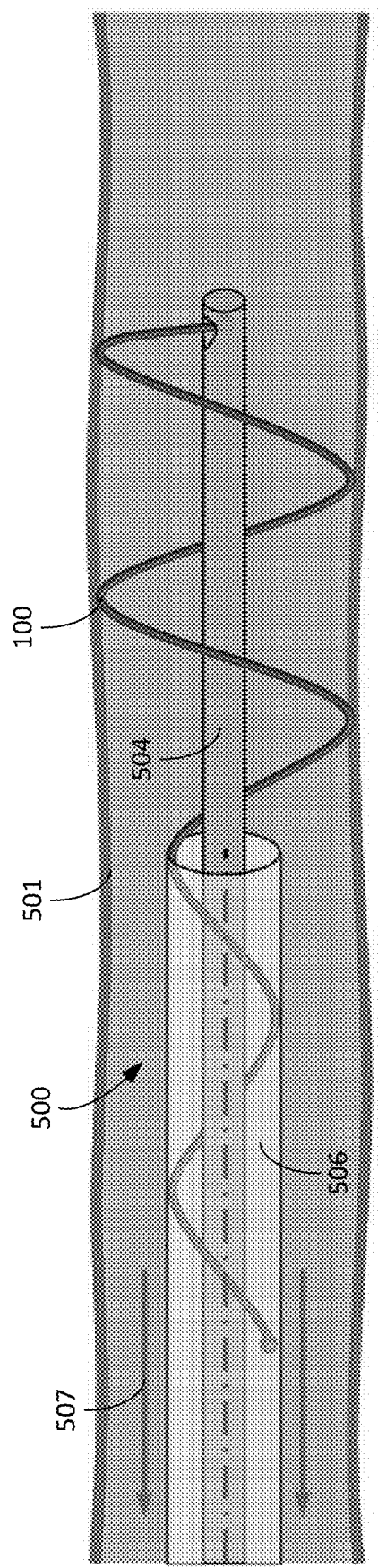
FIG. 5A illustrate a stent and a delivery instrument.

FIG. 4B illustrates a method 410 of delivering the stent into the airway of the patient. The method 410 is an example of a delivery operation (402) as described with respect to FIG. 4A. The method 410 can be performed using a delivery instrument. FIG. 5A illustrates an example of a delivery instrument 500. The delivery instrument 500 can include multiple concentric cannulas. For example, the delivery instrument 500 includes a first cannula 502 (shown in FIG. 5B) and a second cannula 504, with the first cannula 502 being concentric with the second cannula 504. The first cannula 502 can be an innermost cannula, and the second cannula 504 can be arranged around the first cannula 502. The first and second cannulas 502, 504 are adjacent to one another and are longitudinally movable relative to one another.

As shown in FIG. 5A, in some implementations, the delivery instrument 500 can further include a third cannula 506. The first, second, and third cannulas 502, 504, 506 are concentric with one another, and the third cannula 506 is arranged around both the first cannula 502 (shown in FIG. 5B) and the second cannula 504. The third cannula 506 is movable relative to both the first and second cannulas 502, 504. An outer diameter of the third cannula 506 is greater than an outer diameter of the second cannula 504, and the outer diameter of the second cannula 504 is greater than an outer diameter of the first cannula 502. Each of the first, second, and third cannulas 502, 504, 506 can be cylindrical across substantially entire lengths of the first, second, and third cannulas 502, 504, 506, e.g., at least 90%, at least 95%, or at least 99% of the entire lengths of the first, second, and third cannulas 502, 504, 506.

The delivery instrument 500 can be used to deliver the stent 100 into the airway 102 of the patient. First, the first cannula 502 (shown in FIG. 5B) and the second cannula 504 can be moved relative to one another to place the deliver instrument 500 into a lock configuration in which the stent 100 is locked between the first and second cannulas 502, 504. Then, the stent 100, with the first and second cannulas 502, 504 can be retracted into or inserted into the third cannula 506 so that the stent 100 is placed into a compressed state within the third cannula 506. Next, the delivery instrument 500 can be inserted into the airway 102 to position the first, second, and third cannulas 502, 504, 506 and the stent 100 into a desired position within the airway 102. The third cannula 506 can then be retracted (in a direction 507 shown in FIG. 5A) to release the stent 100, thereby allowing the stent 100 to engage with walls of the airway 102. The first and second cannulas 502, 504 finally can be moved relative to another to place the delivery instrument 500 into a release configuration, thereby releasing the stent 100. Example method of delivering the stent 100 using the delivery instrument 500 are described herein with respect to FIGS. 5B-5H.

Referring to FIGS. 5B-5C, the second cannula 504 includes an opening 508. The opening 508 is configured receive a portion of the stent 100. In particular, the opening 508 can receive one of the protruding elements 110, 112 (shown in FIG. 2). The opening 508 further includes a notch 510 that is sized and shaped to receive one of the protruding elements 110, 112 such that, when received in the notch 510, the protruding element does not move relative to the second cannula 504.

Before insertion of the delivery instrument into the airway of the patient, a portion of the stent 100 is inserted into the opening 508. For example, the protruding element 110 on the distal end 114 of the helically arranged structure 104 (shown in FIG. 2) can be inserted into the notch 510 of the opening 508. The delivery instrument 500 is in a release configuration in FIG. 5B in which the protruding element 110 is movable relative to the first cannula 502. As shown in FIG. 5C, the second cannula 504 is movable longitudinally relative to the first cannula 502 toward the stent 100. The second cannula 504, as it is being moved toward the stent 100, abuts the stent 100. The delivery instrument 500 is in a lock configuration in FIG. 5C in which the stent 100 is locked between the first and second cannulas 502, 504, with the second cannula 504 pushing the stent 100 into the first cannula 502 and is locked at the notch 510. The protruding element 110 is held between the first and second cannulas 502, 504, thus inhibiting the protruding element 110 and the stent 100 from moving relative to the first and second cannulas 502, 504. As shown in FIG. 5D, when the delivery instrument 500 is in the lock configuration, the stent 100 is arranged around the first and second cannulas 502, 504. The distal end 114 (shown in FIG. 2) of the helically arranged structure 104 (shown in FIG. 2) is locked between the first and second cannula 502, 504, and the helically arranged structure 104 extends proximally along the first and second cannulas 502, 504, with the first and second cannulas 502, 504 extending through the interior pathway 108 (shown in FIG. 2) of the stent 100.

For example, referring back to FIG. 4B, in the method 410, a delivery instrument is inserted (412) into the airway of the patient. The delivery instrument can be engaged with the stent to allow an operator, e.g., a physician, a nurse, or other medical practitioner, to manipulate the delivery instrument to deliver the stent to the airway of the patient. The stent can be disposed within the delivery instrument before the delivery instrument is inserted into the airway. When the delivery instrument is inserted (412) into the airway of the patient, the stent can be housed within another cannula of the delivery instrument before the stent is delivered into the airway. The delivery instrument is inserted into the airway only after the stent is housed within this cannula. For example, as shown in FIG. 5E, after the delivery instrument 500 is in the lock configuration in which the stent 100 is held between the first and second cannulas 502, 504, the stent 100 is insertable into the third cannula 506 such that the third cannula 506 serves as a housing for the stent 100. The first and second cannulas 502, 504 are inserted into the third cannula 506 with the stent 100 being held between the first and second cannulas 502, 504. In particular, the assembly including the first and second cannulas 502, 504 and the stent 100 is inserted into a proximal end 512 of the third cannula 506. The first and second cannulas 502, 504 and the stent 100 can be inserted into the third cannula 506 with a screwing motion. An entire length of the stent 100 can be positioned within the third cannula 506. The delivery instrument 500, with the stent 100 housed within the third cannula 506, can then be inserted into the airway of the patient.

Referring back to FIG. 4B, after the delivery instrument is inserted (412) into the airway of the patient, an outer cannula of the delivery instrument can then be withdrawn (414) from the airway of the patient. The outer cannula can be an outermost cannula of the delivery instrument. In some implementations, referring to FIG. 5F, the third cannula 506 corresponds to the outer cannula. The third cannula 506 is withdrawn relative to the first and second cannulas 502, 504 and from the airway of the patient such that the third cannula 506 moves proximally and longitudinally relative to the first and second cannulas 502, 504. As the third cannula 506 is withdrawn from the airway, the stent 100 is released from the third cannula 506 and emerges from a distal end 514 of the third cannula 506. Similarly, the first and second cannulas 502, 504 also emerge from the distal end 514. The stent 100 can diametrically expand such that the stent 100 engages the tissue defining the airway as the stent 100 is released from the third cannula 506. The third cannula 506 can be withdrawn through an unscrewing motion. Referring to FIG. 5G, the third cannula 506 can be withdrawn until the entire length of the stent 100 is released from within the interior of the third cannula 506, e.g., until the entire length of the stent 100 is positioned distal to the distal end 514 of the third cannula 506.

Referring back to FIG. 4B, after the outermost cannula of the delivery instrument is withdrawn (414) from the airway of the patient, an inner cannula of the delivery instrument is retracted to release the stent from the delivery instrument. In some implementations, referring to FIG. 5H, the first cannula 502 corresponds to the inner cannula. The first cannula 502 can be retracted relative to the second cannula 504, thereby releasing the protruding element 110 from the delivery instrument 500. In particular, the protruding element 110 is released from the opening 508 and the notch of the second cannula 504. After the stent 100 is released from the delivery instrument 500, the delivery instrument 500, including the first, second, and third cannulas 502, 504, 506, can be withdrawn from the airway.

Figure 4C:
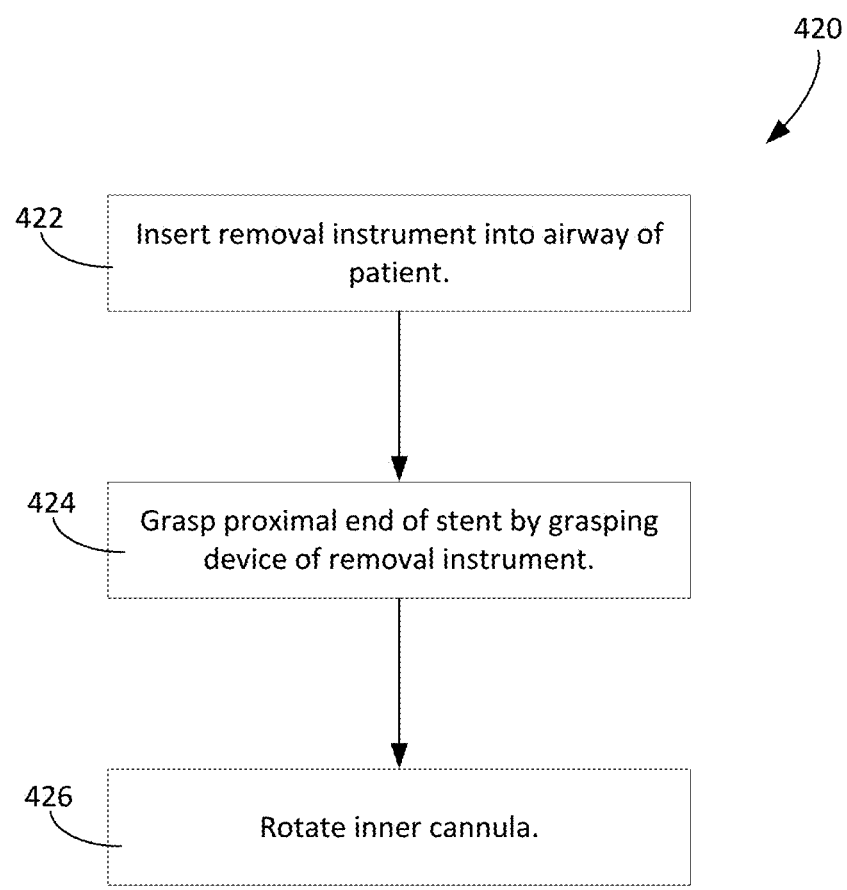
FIG. 4C is a flowchart of a method of removing a stent from an airway of a patient.
Figure 6A:
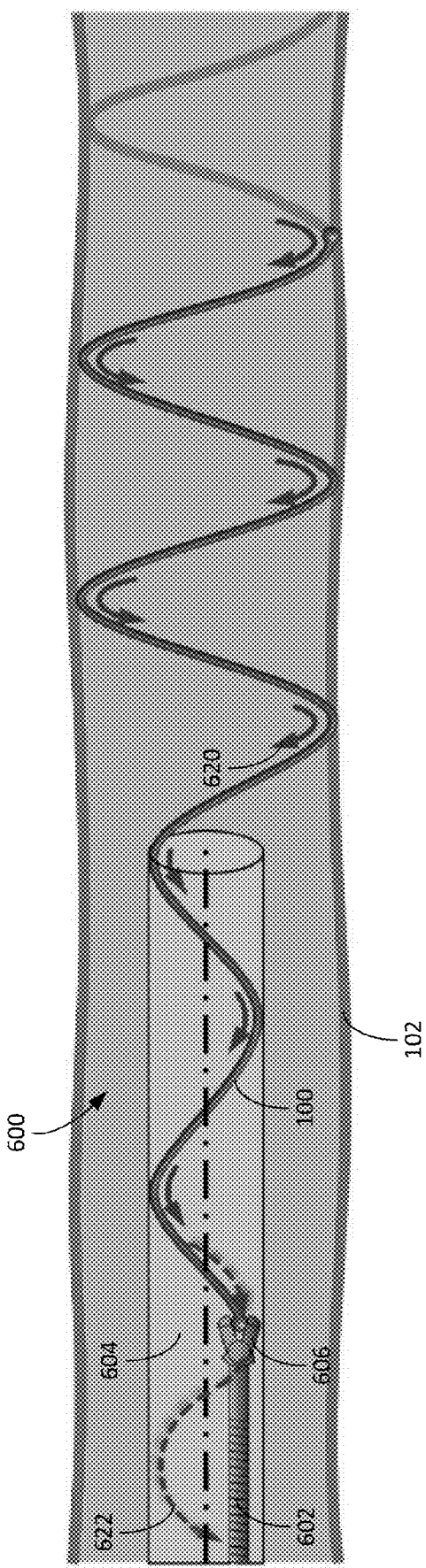
FIG. 6A illustrate a stent and a removal instrument.

FIG. 4C illustrates a method 420 of removing a stent from an airway of a patient. The method 420 is an example of a removal operation (404) as described with respect to FIG. 4A. The method 420 can be performed using a removal instrument. FIG. 6A illustrates an example of a removal instrument 600. The removal instrument 600 can include a cannula 604 and a grasping device 606 attached to a distal end of a shaft 602. To remove the stent 100 from the airway 102, the grasping device 606 is used to grasp an end of the stent 100 and then is retracted or inserted into the cannula 604, thereby retracting the stent 100 into the cannula 604. The retraction or insertion into the cannula 604 is in the form of a twisting movement 620 of the stent 100, which can be effectuated by a rotational movement 622 of the grasping device 606.

In some implementations, the removal instrument 600 can include multiple concentric cannulas. For example, referring to FIG. 6B, the shaft 602 can be a first cannula 602 and the cannula 604 can be a second cannula 604. The grasping device 606 can be connected to the first cannula 602. The grasping device 606 can be, for example, connected to an outer surface of the first cannula 602 and can extend distal to a distal end 603 of the first cannula 602. Many arrangements are possible. For example, the grasping device could alternately be delivered through cannula 602 and may or may not be attached to it. The grasping device 606 can be forceps operable to grasp onto the stent 100 (shown in FIG. 6C). In some implementations, the grasping device 606 includes one or more jaws that are movable relative to one another to grasp the stent 100. The removal instrument 600 includes an actuator 607 that is operable by the operator to open or close the forceps.

The first cannula 602 is concentric with the second cannula 604. The first cannula 602 is an inner cannula, and the second cannula 604 is an outer cannula. The first cannula 602 is positioned within the second cannula 604 and is engaged with the second cannula 604 via a helical joint. In particular, the first cannula 602 can include a threaded coupling 608 engaged with a threaded coupling 610 of the second cannula 604. The threaded coupling 608 and the threaded coupling 610 can have pitches similar to the pitch $p_0$ of the helically arranged structure 104 of the stent 100 (shown in and described with respect to FIG. 2). In some implementations, the pitches of the threaded coupling 608, the threaded coupling 610, and the helically arranged structure 104 are identical or substantially similar to one another, e.g., within 0.1 to 5% of one another. The first cannula 602 and the second cannula 604 are longitudinally movable relative to one another. In particular, the first cannula 602 can be manually rotated at a proximal end 611 of the removal instrument 600, thereby causing the first cannula 602 to move longitudinally relative to the second cannula 604 due to the threaded engagement between the threaded couplings 608, 610.

Figure 6B:
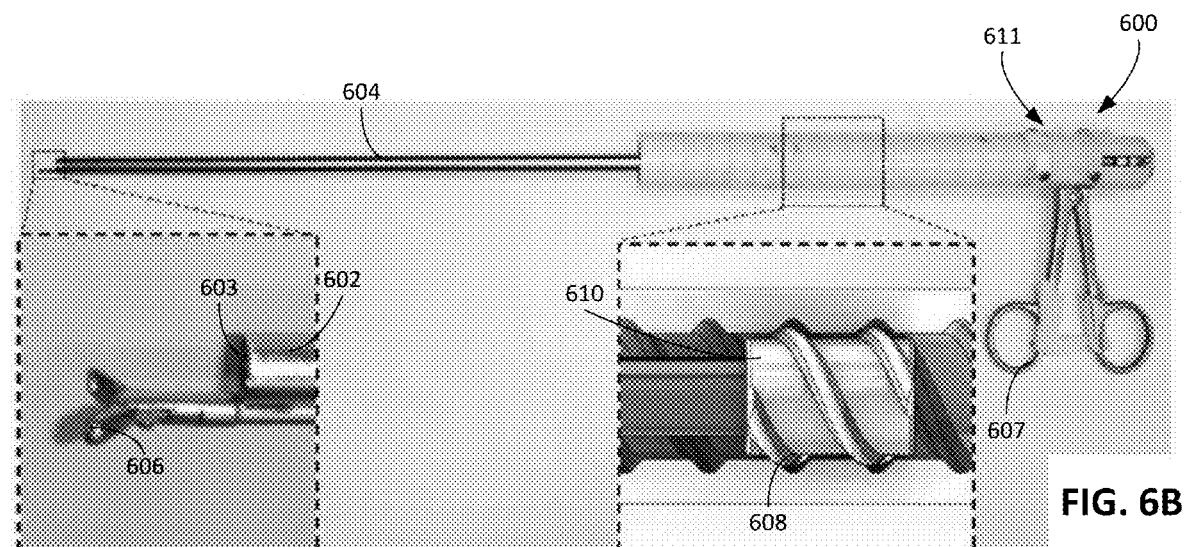
FIGS. 6B-6D illustrate a stent and a removal instrument manipulating the stent.

Referring back to FIG. 4C, in the method 420, the removal instrument is inserted (422) into the airway of the patient. For example, as shown in FIG. 6B, the removal instrument 600, with its first and second cannulas 602, 604 and the grasping device 606, is inserted into the airway of the patient. The first cannula 602 and the attached grasping device 606 can be positioned within the second cannula 604 until a distal end 612 of the second cannula 604 is positioned proximate to the stent 100.

Figure 6C:
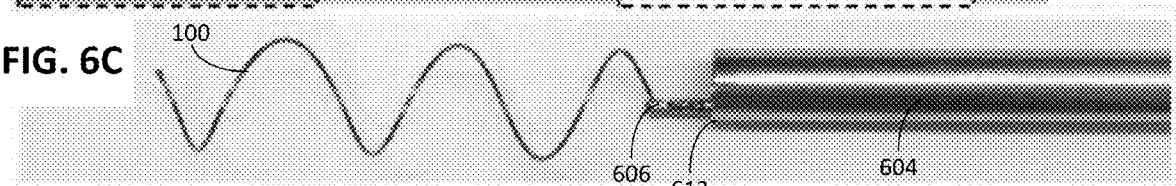

Referring back to FIG. 4C, after the removal instrument is inserted (422) into the airway of the patient, a proximal end of the stent is grasped (424) by a grasping device of the removal instrument. For example, as shown in FIG. 6C, the grasping device 606 can be advanced distally beyond the distal end 612 of the second cannula 604, and then can be actuated using the actuator 607 (shown in FIG. 6B) to grasp the stent 100. The grasping device 606 can be positioned to grasp one of the protruding elements 110, 112 of the stent 100 (shown in FIG. 2). In particular, the grasping device 606 can be positioned to grasp the proximal protruding element 112 positioned on the proximal end of the stent 100.

Figure 6D:
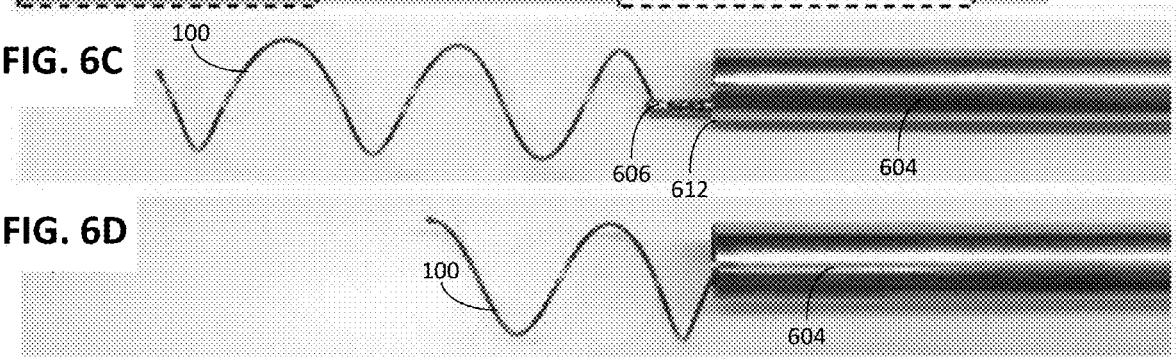

Referring back to FIG. 4C, after the proximal end of the stent is grasped (424) by the grasping device of the removal instrument, an inner cannula of the removal instrument is rotated (426). This rotation can cause the inner cannula to retract into the outer cannula. The grasping device can be connected to the inner cannula such that the grasping device is also retracted into the outer cannula as the inner cannula is rotated. For example, as shown in FIG. 6D, the first cannula 602 (shown in FIG. 6B) can be manually rotated at the proximal end 611 (shown in FIG. 6B) of the removal instrument 600, thus causing the first cannula 602 to rotate relative to the second cannula 604. The threaded engagement between the first cannula 602 and the second cannula 604 causes the first cannula 602 to retract, with the grasping device 606 (shown in FIG. 6C), into the second cannula 604. In addition, because the grasping device 606 is engaged with the stent 100, the stent 100 also retracts into the second cannula 604. The stent 100 is compressed as the stent 100 is retracted into the second cannula 604. The first cannula 602 can be rotated until the entire length of the stent 100 is retracted into the second cannula 604 such that the stent 100 is completely disengaged from the tissue defining the airway of the patient.

Figures 7A, 7B, 7C, 7D:
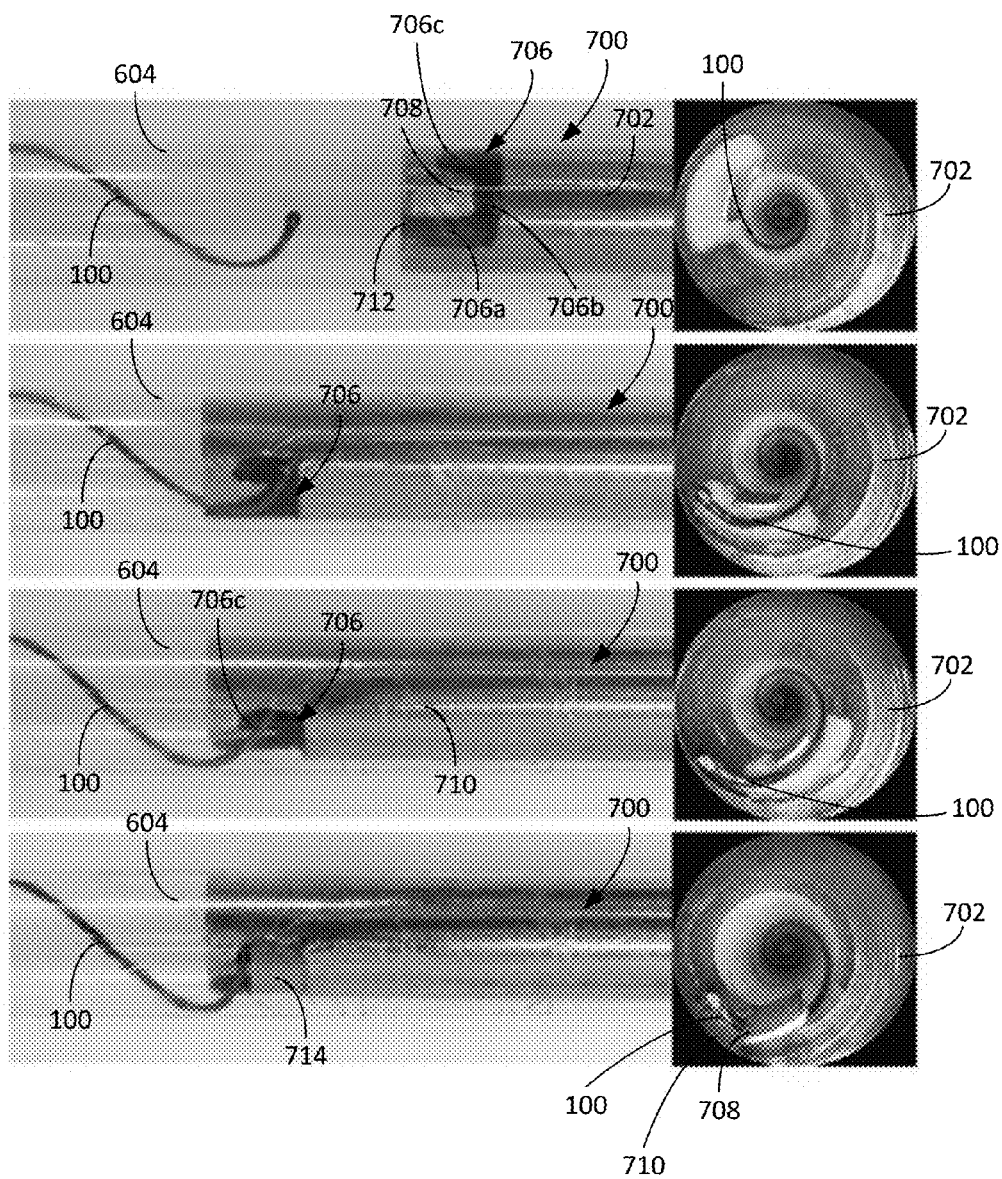
FIGS. 7A-7D illustrate a stent and a grasping instrument manipulating the stent.

In some implementations, during the method 420 described with respect to FIG. 4C, the stent may disengage from the removal instrument as the inner cannula is retracted into the outer cannula. Because the stent is positioned within the outer cannula, it may be difficult to manipulate the grasping device to regrasp the stent. FIG. 7A illustrates a regrasping instrument 700. The regrasping instrument 700 includes a cannula 702. A distal portion of the cannula 702 includes an opening 706 configured to receive a proximal portion of the stent 100. The opening 706 includes a longitudinally extending portion 706a, a circumferentially extending portion 706b, and a notch 706c. The opening 706 is at least partially defined by a scoop member 708 that extends radially inwardly from a cylindrical portion 710 of the cannula 702. The scoop member 708 extends proximally and radially inwardly from a distal end 712 of the cannula 702. Referring briefly to FIG. 7D, the regrasping instrument 700 further includes a cannula 714 positioned within the cannula 702. The cannula 714 is movable longitudinally relative to the cannula 702.

FIGS. 7A-7D show the regrasping instrument 700 being used to regrasp the stent 100, with the left images of FIGS. 7A-7D showing side views of the regrasping instrument 700 and the stent 100, and the right images of FIGS. 7A-7D showing longitudinal view of the regrasping instrument 700 and the stent 100. To regrasp the stent 100 after, for example, the grasping device 606 of the removal instrument 600 (shown in FIG. 6B) loses engagement with the stent 100, the regrasping instrument 700 can be inserted into the removal instrument 600 to regrasp the stent 100. For example, the grasping device 606 and the first cannula 602 (shown in FIG. 6A) can be removed from the second cannula 604 (shown in FIG. 6A) through a proximal portion of the removal instrument 600. The regrasping instrument 700 can then be inserted into the removal instrument 600 and, in particular, the second cannula 604 (shown as transparent in FIGS. 7A-7D). As shown in FIG. 7A, the regrasping instrument 700 is advanced relative to the second cannula 604 toward the stent 100. Then the regrasping instrument 700, as shown in FIG. 7B is advanced and rotated relative to the stent 100 such that the proximal end of the stent 100 is received in the opening 706. The regrasping instrument 700 can be manipulated until the notch 706c of the opening 706 receives the stent 100, as shown in FIG. 7C. Then, the cannula 714 is movable longitudinally relative to the cannula 702 until the cannula 714 engages the stent 100 such that the stent 100 is held between the cannula 702 and the cannula 714 as shown in FIG. 7D. To continue removal of the stent 100 from the airway, the regrasping instrument 700, including the cannula 702 and the cannula 714, can be rotated.

Example Methods of Forming Stents

In some implementations, a stent can be customized to match anatomy of a patient. The stent can be formed within the airway of the patient such that the geometry of the stent matches with the specific geometry of the airway of the patient.

Figure 8:
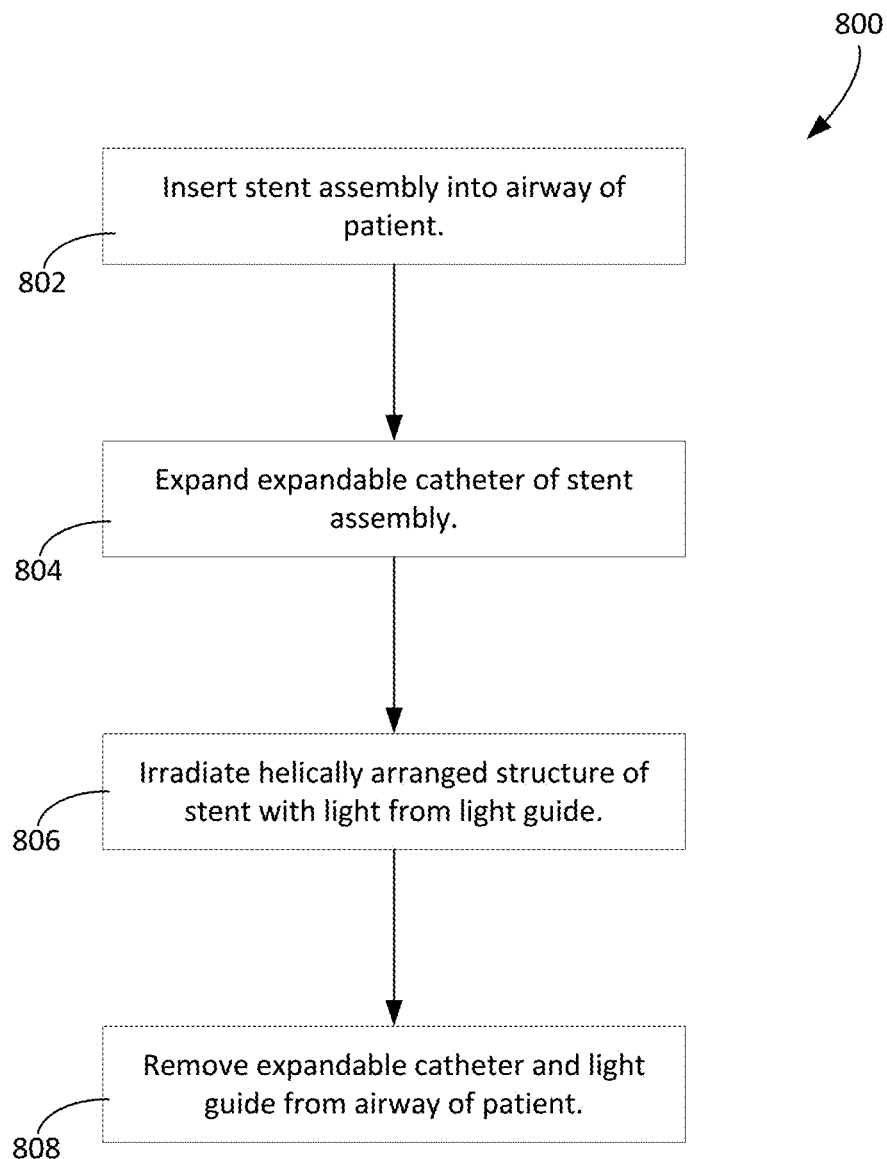
FIG. 8 is a flowchart of a method of forming a stent.
Figure 9A:
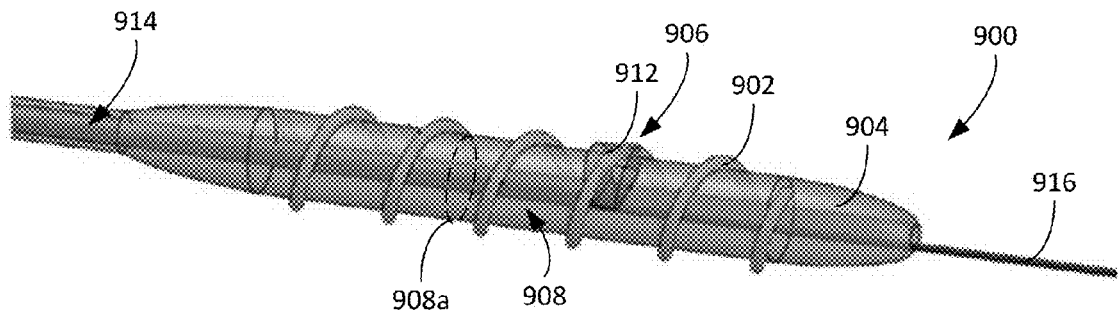
FIGS. 9A-9B illustrate a stent assembly used to form a stent.
Figure 9B:
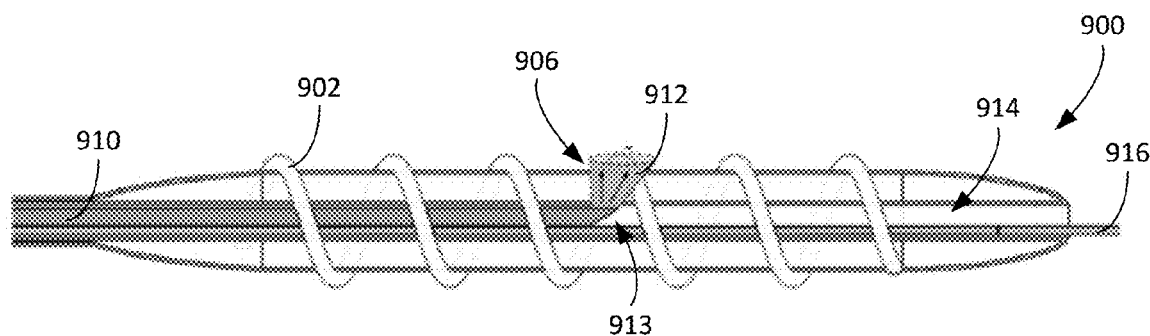

FIG. 8 illustrates an example of a method 800 to form a stent for an airway of a patient. In the method 800, a stent assembly is inserted (802) into an airway of a patient. FIGS. 9A-9B illustrate an example of a stent assembly 900 that can be used to deliver a stent 902 to an airway of a patient and then form the stent 902 according to the airway of the patient. The stent assembly includes the stent 902, an expandable catheter 904, and a light delivery system 906. The stent 902 can be similar to the stent 100 described herein, and can include a helically arranged structure similar to the helically arranged structure 104 of the stent 100. The stent can be any expandable geometry such as a mesh or woven material. The helically arranged structure of the stent 902 can include a light-curable material. For example, the helically arranged structure can include a polymer shell of the stent 902 and the light-curable material, with the light-curable material being positioned within the shell. The polymer shell can be a hollow tube filled with the light-curable material. The stent 902 can define an interior pathway 908 within which the expandable catheter 904 is disposed. The interior pathway 908 can correspond a pathway extending from a first longitudinal end of the stent 902 to a second longitudinal end of the stent 902. A cross-section 908a of the interior pathway 908 can span transversely across an inner diameter of the helically arranged structure 104.

As part of the insertion step (802), the stent assembly can be inserted (802) at a desired location within the airway of the patient. The helically arranged structure of the stent 902 can be wrapped around the expandable catheter 904 during insertion. The expandable catheter 904 can be, for example, a balloon catheter expandable through pressurization. The light delivery system 906 includes a light source (not shown), an optical fiber 910, and a light guide 912. The light guide 912 is disposed in the interior pathway 908 of the stent 902. The light guide 912 can extend through the expandable catheter 904.

The stent assembly 900 further includes a lumen 914 through which a guidewire 916 can be inserted. In some implementations, the stent assembly 900 can be inserted into the airway of the patient via the guidewire 916. The lumen 914 can further accommodate the optical fiber 910 of the light delivery system 906. The lumen 914 can also enable jet ventilation as the stent 902 is being inserted (802).

Referring back to FIG. 8, after the stent assembly is inserted (802) into the airway of the patient, an expandable catheter of the stent assembly is expanded (804). For example, referring also to FIGS. 9A-9B, the expandable catheter 904 is expanded to push the stent 902 into the tissue defining the airway of the patient. The expandable catheter 904 can be inflated through pressurization. An air source (not shown) can deliver air to the expandable catheter 904 to inflate the catheter 904 and hence reshape the stent 902. The expandable catheter 904 can be expanded to stretch the airway of the patient. In some implementations, the expandable catheter can be expanded by 2 to 10 millimeters.

In some implementations, the light guide 912 is part of the optical fiber 910. The light guide 912, for example, can be a feature on a distal end 913 of the optical fiber 910 that directs light radially outwardly from the optical fiber 910. A design of the light guide 912 can vary in implementations that can produce different illumination patterns and intensity distributions. Depending on the spatial distribution of energy, the light guide 912 may be rotated within and translated along the extent of the stent 902 to expose substantially an entirety of stent 902 until cured, e.g., at least 90%, at least 95%, or at least 97% of an inner surface of the stent 902.

Figure 9C:
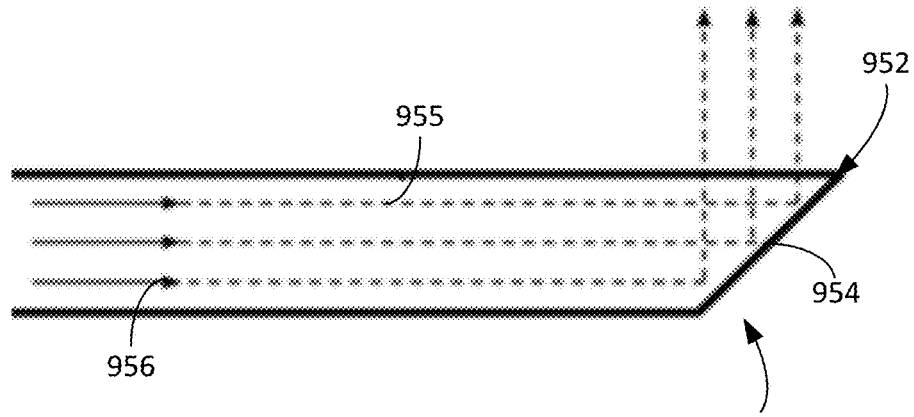
FIGS. 9C-9E illustrate example optical fibers for stent assemblies.
Figure 9D:
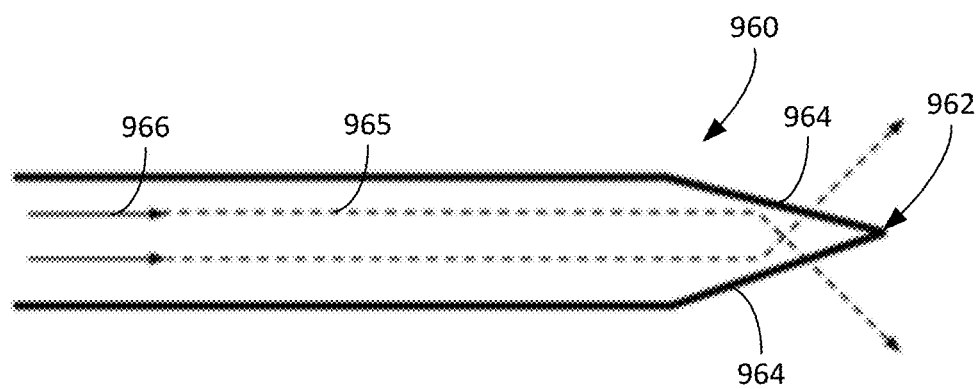
Figure 9E:
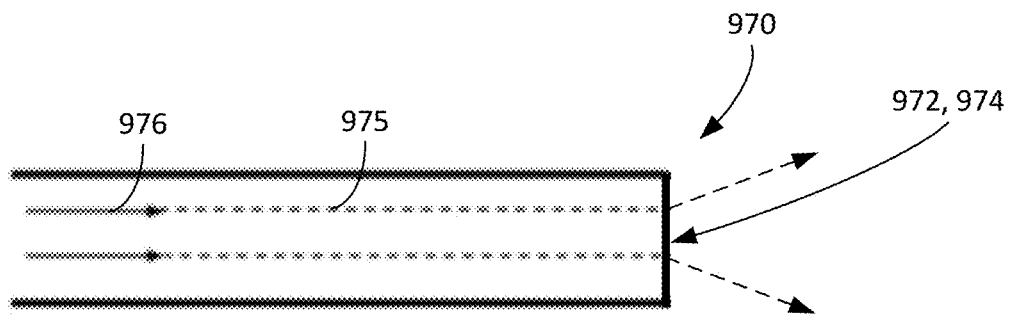

FIGS. 9C-9E show example distal ends of optical fibers 950, 960, 970, respectively. The optical fiber 910 described with respect to FIGS. 9A-9B can include features described with respect to the optical fibers 950, 950. Referring to FIG. 9C, in some implementations, the optical fiber 950 includes a light guide 952 at a distal end of the optical fiber 950. The light guide 952 has a bevel shape including a distal surface 954 angled relative to a longitudinal axis of the optical fiber 950 and thus angled relative to a direction 956 of travel of light 955 transmitted through the optical fiber 950. The distal surface 954 directs the light 955 radially outward in one direction.

Referring to FIG. 9D, in some implementations, the optical fiber 960 includes a light guide 962 at a distal end of the optical fiber 960. The light guide 962 has a conical shape including a distal surface 964. The distal surface 964 form an outer surface of a cone at the distal end of the optical fiber 960. In this regard, the distal surface 964 is angled relative to a direction 966 of travel of light 965 transmitted through the optical fiber 960. The distal surface 964 directs light radially outward in multiple directions, e.g., radially outwardly 360-degrees around distal end of the optical fiber 960.

Referring to FIG. 9E, in some implementations, the optical fiber 970 includes a light guide 972 at a distal end of the optical fiber 960. The light guide 972 can correspond to a flat distal surface 974 of the optical fiber 970. The distal surface 974 is perpendicular to a direction 976 of travel of the light 975 transmitted through the optical fiber 970. Light 975 is transmitted through the optical fiber 970 and outward through the distal surface 974. The beam produced by the light 975 can be substantially conically shaped, e.g., frustoconically shaped.

Referring to FIG. 8, after the stent assembly is expanded (804), a helically arranged structure of a stent of the stent assembly is irradiated (806) with light from the light guide. When the helically arranged structure of the stent is being irradiated (806), the helically arranged structure is cured. In particular, a light-curable material within the helically arranged structure is cured such that the helically arranged structure is formed into the shape of the airway of the patient. For example, referring also to FIGS. 9A-9B, the light guide 912 receives light transmitted through the optical fiber 910 from the light source. When the helically arranged structure of the stent 902 is irradiated with light emitted by the light guide 912, the light-curable material in an interior of the stent 902 is cured. The light source can be operated for a sufficient time to cure substantially all of the material in the interior of the stent 902, e.g., 5 to 120 seconds, 5 to 45 seconds, 30 to 90 seconds, 40 to 80 seconds, 50 to 70 seconds, about 10 seconds, about 20 seconds, about 30 seconds, about 40 seconds, about 50 seconds, about 60 seconds, etc.

In some implementations, to cure the material in the interior of the stent 902, the light guide is positioned at multiple locations relative to the stent 902, and then the stent 902 is irradiated when the light guide is at each of the multiple locations. The light guide can begin at a location proximate to the distal portion of the stent 902, and then can be retracted proximally to one or more locations between the distal portion of the stent 902 and the proximal portion of the stent 902. The light guide, at its final location, can be positioned proximal to the proximal portion of the stent 902. In some cases, the light guide is positioned in two different locations relative stent 902, at a first location proximal to the distal portion of the stent 902 to cure the material in the distal portion of the stent 902 and at a second location proximal to the proximal portion of the stent 902 to cure the material in the proximal portion of the stent 902. The light source can be activated for a sufficient time to cure substantially all of the material in the portion of the stent 902 being irradiated, e.g., 5 to 120 seconds, 5 to 45 seconds, 30 to 90 seconds, 40 to 80 seconds, 50 to 70 seconds, about 10 seconds, about 20 seconds, about 30 seconds, about 40 seconds, about 50 seconds, about 60 seconds, etc. Referring to FIG. 8, after the stent assembly is irradiated (806), the expandable catheter and the light guide are removed (808) from the airway of the patient. In some implementations, before the expandable catheter and the light guide are removed (808), the expandable catheter is deflated to disengage the expandable catheter from the stent. Thus when the expandable catheter is removed (808) from the airway of the patient, the stent remains in place. For example, referring to FIGS. 9A-9B, after the stent 902 is irradiated such that its light-curable material is cured, the expandable catheter 904 is deflated and disengaged from the stent 902. The expandable catheter 904 and the light guide 912 are then withdrawn from the airway of the patient and withdrawn relative to the stent 902.

The airway of the patient can vary in diameter along a length of the airway, and the stent 902, when cured, can have a non-uniform diameter along its length. For example, the airway may contain constrictions that can vary the diameter of the airway. The stent 902 can accommodate this variation in diameter by expanding to contact the inner wall of the airway and match the geometry of the inner wall of the airway. When cured, the outer diameter of the stent 902 can vary along its length based on the inner diameter of the airway.

The stent 902 can be formed in a number of ways. In some implementations, the stent 902 can be a biocompatible polymer shell in the shape of the stent that is filled with a photocurable liquid polymer prior to delivery of the stent 902 into the airway. The shell can be made of silicone tubing or can be fabricated using soft lithography techniques. For example, a polymer tubing can be used to form an outer surface of the stent 902. The polymer tubing can be formed into a helical shape using a heating and deformation process. A light-curable material can then be inserted into the polymer, e.g., by means of injection with a syringe. Ends of the polymer tubing can be sealed to prevent the light curable material from leaking out of the polymer tubing. To allow a position to be determined using radiological techniques, the ends of the polymer tubing can be sealed with devices that include metal. For example, the devices can be radiopaque. In some implementations, the devices can be screws or pins inserted into the ends of the polymer tubing to seal the ends.

Alternative Implementations

A number of implementations have been described. Nevertheless, it will be understood that various modifications may be made. Accordingly, other implementations are within the scope of the claims.

The stents are described as being used for airways of both pediatric and adult patients. The airways that these stents can be used to support can include the trachea, the bronchi, or the larynx. In addition, the stents are described as being used to treat malacia of airways. In some implementations, the stents can be used to treat other respiratory conditions in which an airway of a patient becomes constricted.

While the helical angle of the helix along which the helically arranged structure 104 extends is described as being between 15 and 35 degrees, the angle may vary in implementations. In some implementations, the helical angle can be less than 15 degrees, while in other implementations, the helical angle can be greater than 35 degrees.

While the protruding elements 110, 112 described with respect to FIG. 2 are described and shown as being on distal and proximal ends of the helically arranged structure 104, in some implementations, these protruding elements 110, 112 can be positioned elsewhere along the helically arranged structure 104. In some implementations, the stent 100 includes only one protruding element, whereas in other implementations, the stent 100 includes three or more protruding elements. In some implementations, a protruding element is positioned distal to the proximal end of the helically arranged structure 104, or is positioned proximal to the distal end of the helically arranged structure 104.

The helix along which the helically arranged structure 104 is described as having a pitch $p_0$ and a diameter $d_0$. In some implementations, a pitch or an outer diameter of the helically arranged structure 104 is uniform across an entire length of the helically arranged structure 104. In some implementations, the pitch or the outer diameter of the helically arranged structure 104 varies along the length of the helically arranged structure 104. For example, the outer diameter can increase or decrease from a proximal end to a distal end of the helically arranged structure 104. Additionally or alternatively, the windings of the helically arranged structure 104 can be positioned increasingly or decreasingly closely to one another from a proximal end to a distal end of the helically arranged structure 104.

In some implementations, in the delivery method 410, removal method 420, method 800, or other methods, an imaging device, such as an endoscope or a medical telescope, can be used to visualize the airway and the stent during delivery, removal, or other manipulation of the stent. For example, during a delivery method, the imaging device can be inserted into one of the cannulas 502, 504, 506 of the delivery instrument 500. In some implementations, the imaging device is inserted into an innermost cannula of the delivery instrument 500, e.g., the first cannula 502. Similarly, during a removal method, the imaging device can be inserted into one of the cannulas 602, 604 of the removal instrument 600. In some implementations, the imaging device is inserted into an innermost cannula of the removal instrument 600 or a cannula connected to the grasping device 600, e.g., the first cannula 602.

In some implementations, the delivery instrument 500, the removal instrument 600, and the regrasping instrument 700 can be part of the same device. For example, the removal instrument 600 and the regrasping instrument 700 could be part of the same device such that the first cannula 602 need not be removed from the second cannula 604 before the regrasping instrument 700 is inserted into the removal instrument 600.

In some implementations, with respect to the delivery instrument 500 described with respect to FIGS. 5A-5G, the first cannula 502, the second cannula 504, or both can be configured to receive an imaging device to allow imagery to be captured during delivery of the stent 100. In some implementations, with respect to the removal instrument 600 described with respect to FIGS. 6A-6C, the first cannula 602, the second cannula 604, or both can be configured to receive an imaging device to allow imagery to be captured during removal of the stent 100. The imaging device can be a bronchoscope.

The material of the stent can vary in implementations. In some implementations, the stent 100 can be formed of a metallic material, such as a nickel-titanium alloy (NiTi) or other biocompatible metal. In some implementations, the stent, e.g., the stent 902, can be formed from a polymer material, a light-curable material, or a combination thereof.

While the stent 902 formed through curing is described as having a helically arranged structure, in some implementations, the stent 902 can have other structures. For example, in some implementations, the stent 902 can have a mesh or woven structure. The mesh or woven structure can be expandable into the tissue of the airway. In some implementations, the mesh or woven structure can further include radial openings, while in other implementations, the mesh or woven structure does not include radial openings, e.g., the mesh or woven structure can be solid.

While the stent 902 is described as including light-curable material, in some implementations, the stent 902 includes curable material that can be cured through methods besides light-based curing. For example, the curable material can include heat-curable material. The stent assembly 900 can include a heat delivery mechanism configured to deliver heat through the expandable catheter 904 to the stent 902, thereby curing the heat-curable material in the stent 902. In some implementations, the stent 902 can include multiple materials that are configured to cure when mixed with one another. The stent 902, for example, can include multiple distinct compartments, each filled with only one of the multiple materials. When the stent 902 is expanded, e.g., by the expandable catheter 904, walls between the compartments break such that the multiple materials can mix one another, thereby initiating the curing process.

Figure 10A:
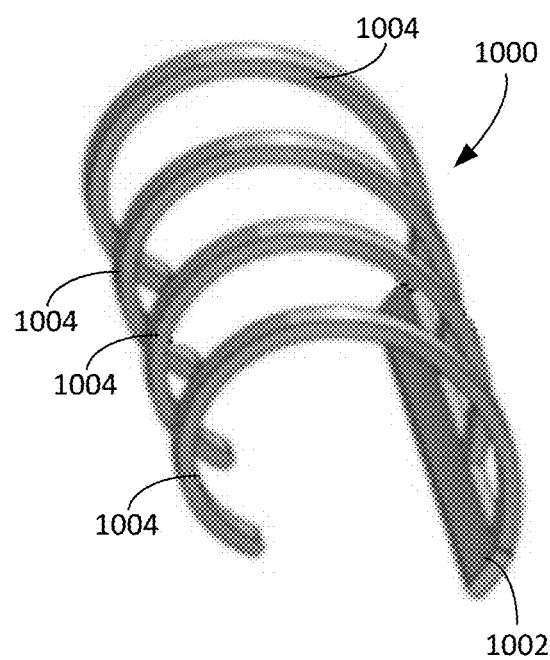
FIG. 10A is a perspective view of another example of a stent.
Figure 10B:
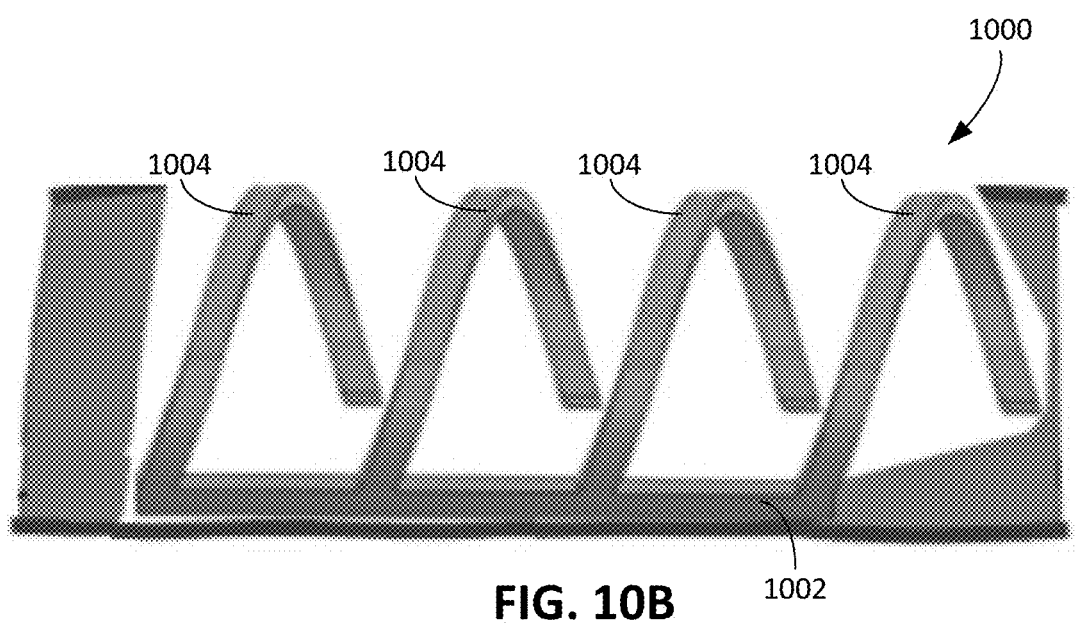
FIG. 10B is a schematic view of the stent of FIG. 10A in an airway of a patient.

While the helically arranged structure 104 of the stent 100 is described as including a helical wound wire, in some implementations, the helically arranged structure 104 includes multiple helically arranged members that do not form a continuous helix. Each of the helically arranged members are arranged on a single helix but do not form a continuous helix. For example, referring to FIGS. 10A-10B, a stent 1000 includes an elongated spine 1002 oriented along a length of the stent 1000. Multiple helically arranged arches 1004 are attached to the spine 1002. The arches 1004 extend along but do not form a continuous helix. The arches 1004 are connected to one another via the spine 1002. First ends of the arches 1004 are attached to the spine 1002, and second ends of the arches 1004 are free. The second ends are spaced apart from the spine 1002.

Figure 11:
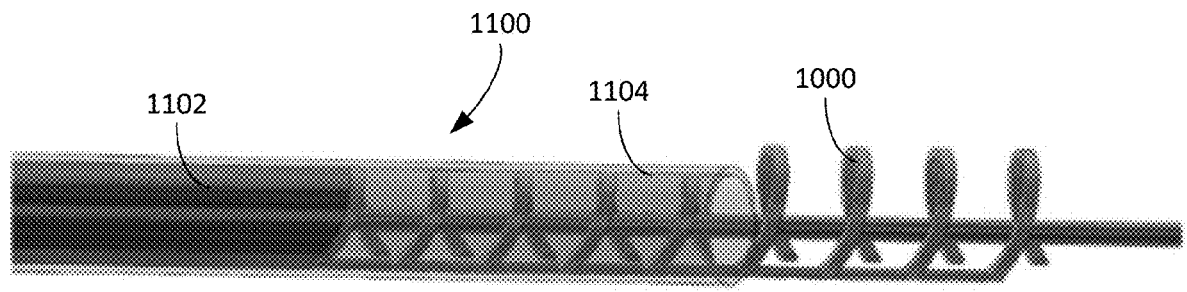
FIG. 11 illustrates the stent of FIG. 10A and a delivery instrument manipulating the stent.

The stent 1000 can be delivered to the airway of the patient in a manner similar to the manner that the stent 100 is described as being delivered to the airway. Alternatively, referring to FIG. 11, the stent 1000 can be delivered using a delivery instrument 1100 including multiple cannulas. The delivery instrument 1100, for example, can include a first cannula 1102 and a second cannula 1104. The first and second cannulas 1102, 1104 are movable relative to one another. The first cannula 1102 is positioned within the second cannula 1104. The delivery instrument 1100 is similar to the delivery instrument 500 described with respect to FIGS. 5A-5G, except that the stent 1000 is loaded into the delivery instrument 1100 in a different manner. To deliver the stent 1000 to an airway of a patient, the stent 1000 can be placed within the second cannula 1104. The stent 1000 is positioned such that its spine 1002 abuts the first cannula 1102. The delivery instrument 1100 with the stent 1000 loaded within the second cannula 1104 can be inserted into the airway of the patient. To release the stent 1000 from the second cannula 1102, the second cannula 1104 can be retracted relative to the first cannula 1102 to release the stent 1000 from the delivery instrument 1100.

Figure 12:
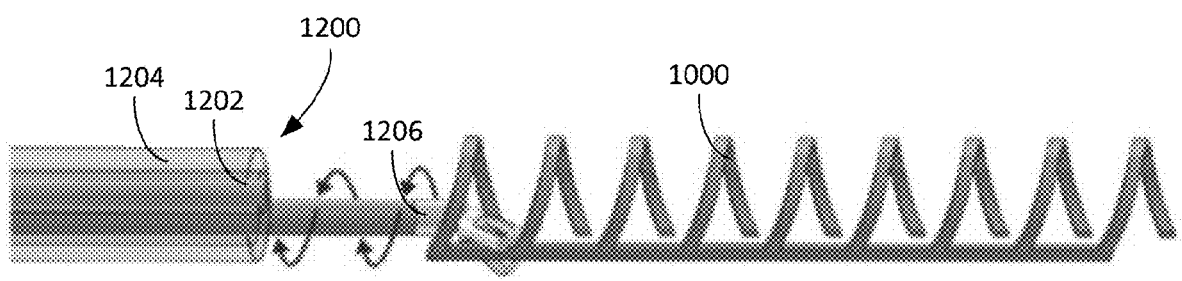
FIG. 12 illustrates the stent of FIG. 10A and a removal instrument manipulating the stent.

The stent 1000 can also be removed from the airway of the patient in a manner similar to the manner that the stent 100 is described as being removed from the airway. Alternatively, referring to FIG. 12, the stent 1000 can be removed using a removal instrument 1200 including multiple cannulas. The removal instrument 1200 can include a first cannula 1202, a second cannula 1204, and grasping device 1206. The removal instrument 1200 is similar to the removal instrument 600 described with respect to FIGS. 6A-6C, except that the grasping device 1206 grasps the spine 1002 of the stent 1000 rather than a protruding element 110, 112.

EXAMPLES

Certain aspects are further described in the following examples, which do not limit the scope of the claims.

Example 1: Idealized Model of Stent Including Helical Arranged Structure

Two airway mucus flow patterns have been observed in humans. The first favors linear transport along the posterior tracheal wall while the second follows a spiral pattern. A stent can be designed so as to reduce the risk that the stent obstructs flow. A helical stent geometry of the appropriate chirality and pitch may be less likely to impede mucus flow for those with a spiral pattern. Furthermore, analogous to a screw, this geometry can resist migration while also enabling atraumatic removal in the case of endothelialization via an unscrewing motion. While a helical stent might interrupt mucus flow for those with linear transport patterns, the width of the interruption can be small as long as the wire diameter used to construct the stent is small.

The design of a helical stent can involve selecting the wire diameter large enough and the helical pitch small enough to provide radial support equivalent to positive pressure ventilation. At the same time, the minimum wire diameter and maximum pitch satisfying the equivalent support criterion can be used to reduce interference with mucus streaming while also introducing the minimum amount of foreign material into the airways.

In other words, pairs of minimum wire diameter and maximum pitch for which the airway cross-sectional area is reduced by an acceptable value when the trachea experiences an external pressure equivalent to positive pressure ventilation can be determined. To determine these diameters and pitches, the reduction in stented airway cross sectional area in response to an external pressure can be determined in an idealized model. In the idealized model, an airway with uniform tissue without reinforcing cartilage rings is assumed. The reduction in cross sectional area can be attributed to two components. First, the external pressure causes the stent to reduce in diameter. Second, the tissue between helical coils stretches to form an asymmetrical hourglass shape. Both of these phenomena can be derived to inform the stent design. In this example, an analytical model for stent deformation is derived.

Stent diameter can be derived as a function of uniform external pressure. Referring back to FIG. 3B, an unloaded pitch and helix diameter are represented as $p_0$ and $d_0$, respectively. When a helix made of a linearly elastic material is compressed radially, its central portion (away from the ends) remains helical, but its pitch and length increase. While the ends deviate from a helical shape, stents can be sized such that they extend on both ends beyond the portion of the airway that requires support. Only the central helical portion is considered in the model below.

Figure 13A:
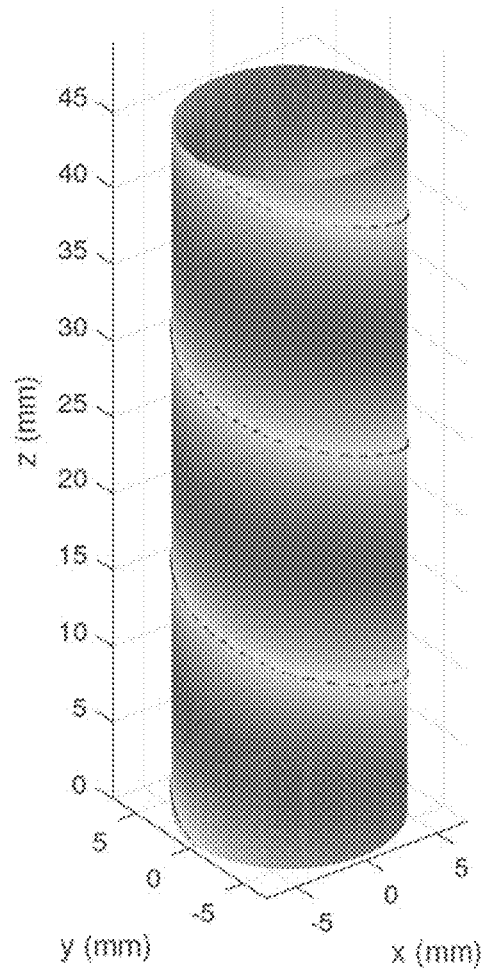
FIGS. 13A-13B illustrate models of a stented trachea in unloaded and loaded states, respectively.
Figure 13B:
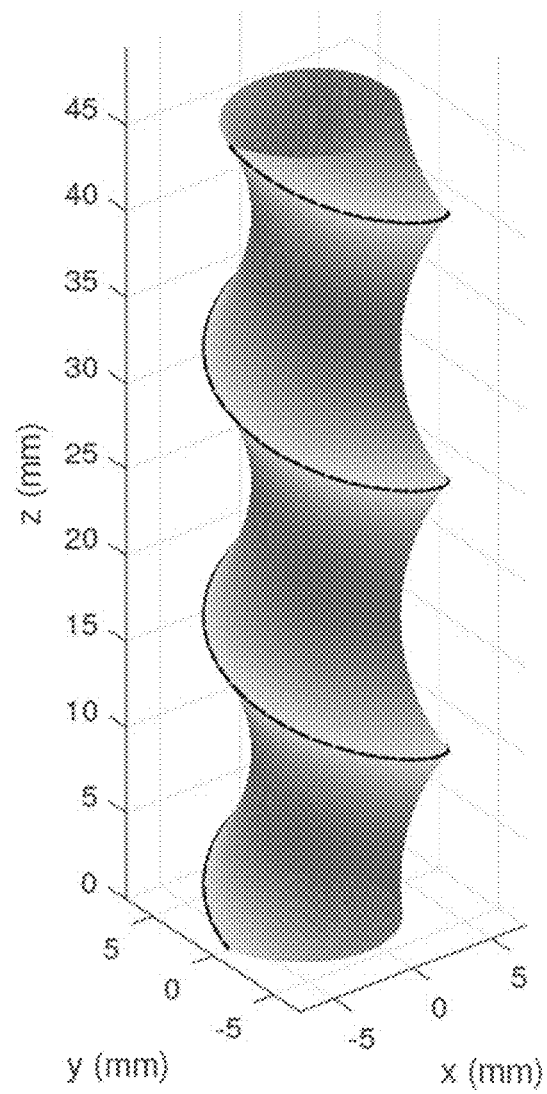

The derivation proceeds in two steps. Given an initial helical elastic stent, a method to solve for the pitch, $p$, associated with a reduced diameter, $d<d_0$ is derived. Next, the pressure associated with a reduced diameter is derived under the assumption that the pressure, $\rho$, is distributed uniformly and can be converted into a radially directed force per unit length, $f$, as shown in FIGS. 13A-13B. In particular, FIGS. 13A-13B show the idealized deformation of a stented trachea under external pressure, with FIG. 13A showing an unloaded stent and trachea, and FIG. 13B showing that under pressure, stent diameter decreases and tracheal tissue is stretched inward.

Figure 14A:
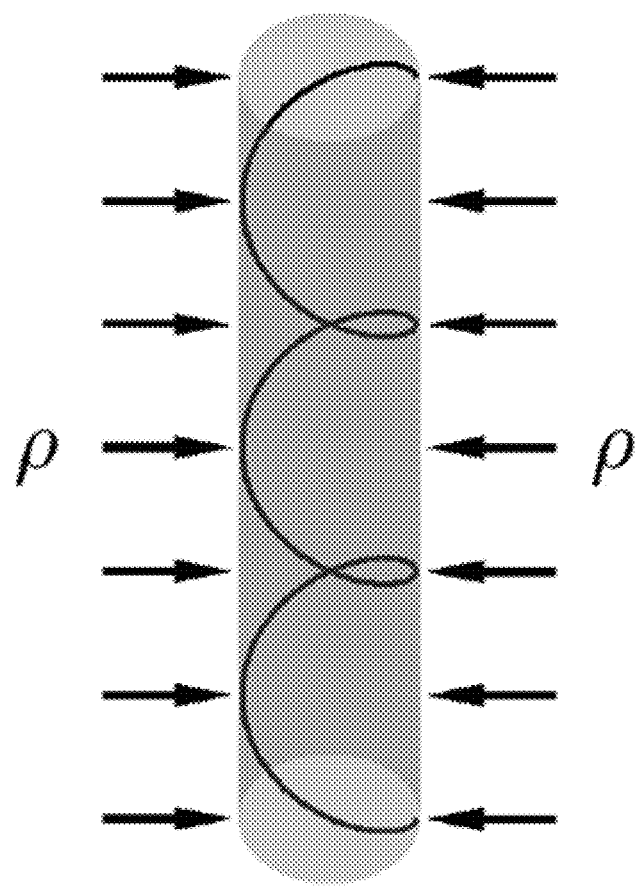
FIG. 14A schematically depicts a stented trachea under a pressure.
Figure 14B:
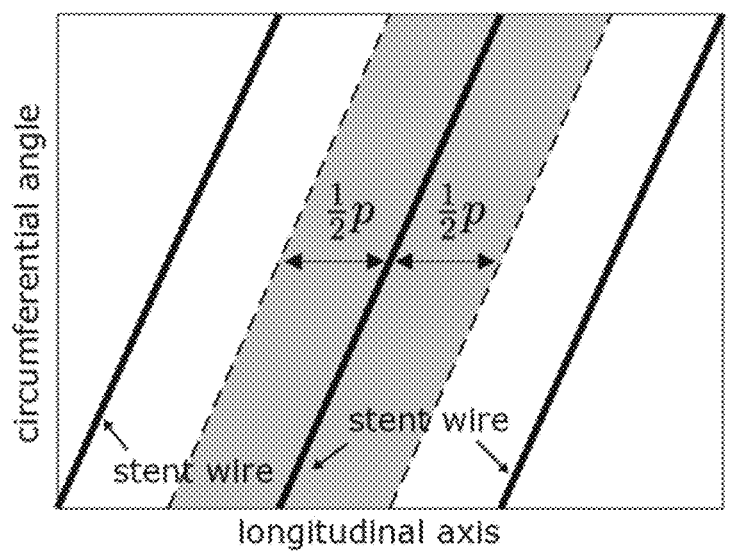
FIG. 14B is a graph illustrating a portion of a trachea supported by a portion of a stent.

FIGS. 14A-14B illustrate the relationship between external pressure and force per unit length on a helical wire. FIG. 14A shows a uniform pressure, $\rho$, applied to a cylindrical trachea supported by a helical stent. FIG. 14B shows a cylindrical coordinate graph showing area under pressure supported by single coil. The conversion to f is given by dividing the pressure integration in the shaded area of FIG. 14B by the length of the stent coil that supports the pressure:

$$f = \frac{p\pi dp}{\sqrt{p^2 + \pi^2 d^2}} \quad (1)$$

A relationship between pitch and diameter can also be derived. The stent wire is parameterized with an arc length parameter $s \in [0, 1]$ where $l$ is the total length of the wire. Let $r(s) \in \mathbb{R}^3$ denote the central line of the wire and $R(s) \in SO(3)$ denote a body frame attached at s where SO(3) is the special orthogonal group, i.e., R(s) is a 3×3 matrix satisfying $R(s)^T R(s) = I_{3\times 3}$ and $\det(R(s))=1$. The body frame R(s) is defined to have its z-axis tangent to the wire and its x-axis point to the center of the helix. The differential equations for R(s) and r(s) are then given by:

$$\dot{R}(s) = R(s)[\hat{u}]$$

$$\dot{r}(s) = R(s)e_z \quad (2)$$

where $e_z = [0\ 0\ 1]^T$ and the upper dot represents the derivative with respect to s. The notation $[\cdot]$ is the 3×3 skew symmetric matrix representation of 3-dimensional vector and the curvature vector it $\hat{u} \in \mathbb{R}^3$ is given by $$\hat{u} = [\hat{u}_x\ \hat{u}_y\ \hat{u}_z]^T = \left[0\ \frac{2\pi^2 d_0}{c_0^2}\ \frac{2\pi p_0}{c_0^2}\right]^T \quad (3)$$

where $c_0 = \sqrt{\pi^2 d_0^2 + p_0^2}$ is the length of a single coil.

Now consider that the helix has a reduced diameter $d(<d_0)$. Assuming the reduced shape is also a helix, its new parameters can be obtained through potential energy minimization. Let $p(>0)$ denote the new helix pitch and c and $u \in \mathbb{R}^3$ denote the corresponding coil length and curvature vector, respectively, given by $$c = \sqrt{\pi^2 d^2 + p^2} \quad (4)$$

$$u = [u_x\ u_y\ u_z]^T = \left[0\ \frac{2\pi^2 d}{c^2}\ \frac{2\pi p}{c^2}\right]^T \quad (5)$$

The change in elastic potential energy is given by $$E = \tfrac{1}{2}\int_0^1 (u-\hat{u})^T K (u-\hat{u}) ds = \tfrac{1}{2}(u-\hat{u})^T K (u-\hat{u}) \quad (6)$$

Where $K \in \mathbb{R}^{3\times 3}$ is a stiffness matrix whose diagonal components consist of the bending stiffness $k_b$ and the torsional stiffness $k_t$, i.e., $$K = \begin{bmatrix} k_b & 0 & 0 \\ 0 & k_b & 0 \\ 0 & 0 & k_t \end{bmatrix} \quad (7)$$

Since d is given, the only unknown in the energy function (6) is p as l, û and K are known and u is a function of d and p. Substituting equation (4) and equation (5) into equation (6), the first-order necessary condition for minimization of E is $$\frac{dE}{dp} = \frac{2\pi l}{c^6}(a_0 + a_1 p + a_2 p^2 + a_3 p^3 + a_4 p^4) = 0 \quad (8)$$

where (9)

$a_0 = -k_t \hat{u}_z \pi^4 d^4,\ a_1 = 2\pi^3 d^2 (k_t - 2k_b + k_b \hat{u}_y d),$
$a_2 = 0,\ a_3 = 2\pi(k_b \hat{u}_y d - k_t),\ a_4 = k_t \hat{u}_z.$ Since $2\pi l/c^6$ is positive, the forth-order polynomial in equation (8) should be zero. The energy-minimizing pitch is one of the four roots of the polynomial, which can be efficiently computed as an eigenvalue problem. The pitch can be selected as the positive real root that minimizes the energy function, E.

A relationship between the reduced helix diameter, d, and an externally applied pressure, ρ (FIG. 14A) can be derived. The relationship between pressure and force per unit length on the wire is given by equation (1). Defining $f \in \mathbb{R}^3$ as the distributed force expressed in the body frame of the helix, the curvature of the reduced diameter helix, u, satisfy the following differential equation from Cosserat rod theory:

$$\begin{bmatrix} \dot{m} \\ \dot{n} \end{bmatrix} = -\begin{bmatrix} 0_{3 \times 1} \\ f \end{bmatrix} - \begin{bmatrix} [u] & \hat{e}_z \\ 0_{3 \times 3} & [u] \end{bmatrix} \begin{bmatrix} m \\ n \end{bmatrix} \quad (10)$$

Here, $m \in \mathbb{R}^3$ and $n \in \mathbb{R}^3$ are the force and moment acting on the helix cross section, respectively. The dot denotes the derivative with respect to arc length, s. Since m is a constant vector given by $m = [0 \; m_y \; m_z]^T = K(u - \hat{u})$, the upper part of equation (10) reduces to $$0_{3 \times 1} = \begin{bmatrix} -u_z m_y + u_y m_z - n_y \\ n_x \\ 0 \end{bmatrix} \quad (11)$$

where $n_y$ and $n_z$ are y and z components of n. Given $n_x = 0$ and $n_y = -u_z m_y + u_y m_z$ by equation (11), the lower part of equation (10) simplifies to $$\begin{bmatrix} 0 \\ 0 \\ \dot{n}_z \end{bmatrix} = -\begin{bmatrix} f_x \\ f_y \\ f_z \end{bmatrix} - \begin{bmatrix} -u_z n_y + u_y n_z \\ 0 \\ 0 \end{bmatrix} \quad (12)$$

Neglecting friction between trachea and the stent, the z component of the contact force, $f_z$, is zero as the z direction of R(s) is always perpendicular to the contact force. Then $f_x = u_z n_y - u_y n_z$, $f_y = 0$ and $n_z$ is constant with respect to arc length. Since all the contact forces on the helix are perpendicular to the central axis of the helix, the force n, which is an integration of the contact forces, should also lie on a plane perpendicular to the helix central axis. Then $n_z$ is dependent on $n_y$ and the helix angle θ:

$$n_z = -n_y \cot \theta \quad (13)$$

substituting $$\cot \theta = \frac{\pi d}{p}$$

and equation (5) into equation (13) yields $$n_z = -n_y \frac{u_y}{u_z}. \quad (14)$$

Combining equations (11), (12) and (14), the contact force f is given by $$f = [f_x \; 0 \; 0]^T \quad (15)$$

where $$f_x = \frac{u_y^2 + u_z^2}{u_z}((k_t - k_b)u_y u_z - k_t \hat{u}_z u_y + k_b \hat{u}_y u_z). \quad (16)$$

Recalling equation (1), the distributed force relates to pressure by $$f = \frac{\rho \pi d p}{\sqrt{p^2 + \pi^2 d^2}} \quad (17)$$

The reduced diameter d can be computed by equating the two force equations (16) and (17). This gives a root finding problem, which can be solved by a standard method, e.g. Newton-Raphson, with the initial guess given by $d = d_0$. This model enables estimation of the changes in diameter and pitch associated with an externally applied pressure. To estimate the reduction in cross-section area due to stretching of the tracheal tissue, a phantom model is used as described in Example 2 below.

Example 2: Estimating Tracheal Airway Reduction in a Phantom Model

In this section, the idealized model of Example 1 is validated. In these experiments, the stented phantom trachea were subjected to 10 cm $H_2O$ pressure and the reduction in cross sectional area of both the stent and the tracheal phantom were measured. The goal was to solve for the pairs of minimum wire diameter and maximum pitch for which airway area is reduced by an acceptable value under tracheal pressure equivalent to positive pressure ventilation. To match the airway of the 20 kg pig used in our in vivo experiment, stenting a 10 cm length of 12 mm diameter trachea is considered. In order to avoid stent migration, the stent outer diameter is chosen to be 2 mm greater than the tracheal diameter.

The stents were fabricated from NiTi wire for its biocompatibility and super elasticity. The set of stent parameters to be tested was selected as follows. To minimize the effect on mucus transport, two readily-available NiTi wire diameters less than 1 mm (0.38 and 0.51 mm) were selected. The model of Section IIA was then used to solve for the practical range of pitches to be considered. To solve for the maximum pitch, the pitch for the smaller wire diameter that would result in a 30% reduction in cross sectional area under 10 cm $H_2O$ pressure was computed. The minimum pitch that resulted in a difference in cross sectional area of less than 5% for the two wire diameters under the same radial pressure was selected This range was used since larger pitches would result in too much airway collapse while smaller pitches, which are less desirable for mucus transport, would produce similar results for the two wire diameters. The minimum and maximum pitches obtained in this way corresponded closely to helix angles of 15° and 35°, respectively. Consequently, stents with helix angles of {15°, 20°, 25°, 30°, 35°} were designed. This resulted in 10 stents with the following parameters:

$d_{wire} \in \{0.38 \text{ mm}, 0.51 \text{ mm}\}$
$d_0 = 12.7 \text{ mm} + d_{wire}$,
$p_0 \in \{10.7 \text{ mm}, 12.5 \text{ mm}, 18.6 \text{ mm}, 23.0 \text{ mm}, 27.9 \text{ mm}\}$.

Figure 15:
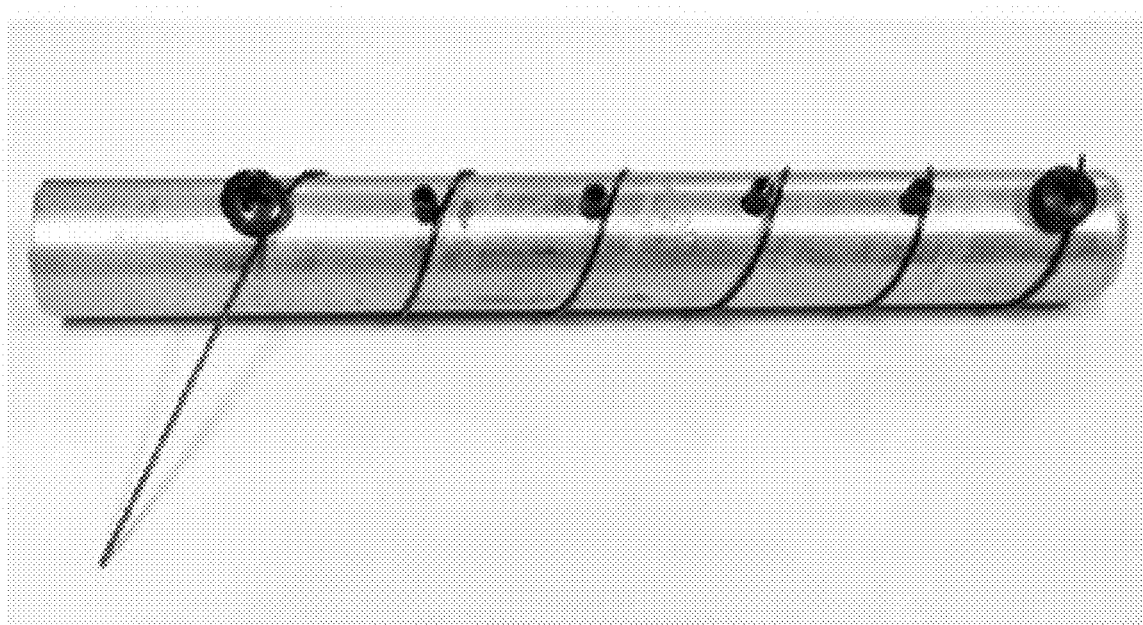
FIG. 15 illustrates a wire wound on a cylindrical support rod.

FIG. 15 illustrates an assembly for stent fabrication, in which NiTi wire is wound and fixed on a cylindrical template of a desired diameter. The stents were shape set from NiTi wire using a template as shown in FIG. 15 by heating to 520 degrees Celsius for 30 minutes followed by immediate quench in room temperature water. To minimize airway trauma and to assist in delivery and removal, the ends of the helix are spherical balls formed by melting the wire with a TIG welder, similar to the protruding elements shown in FIG. 2.

Figure 16:
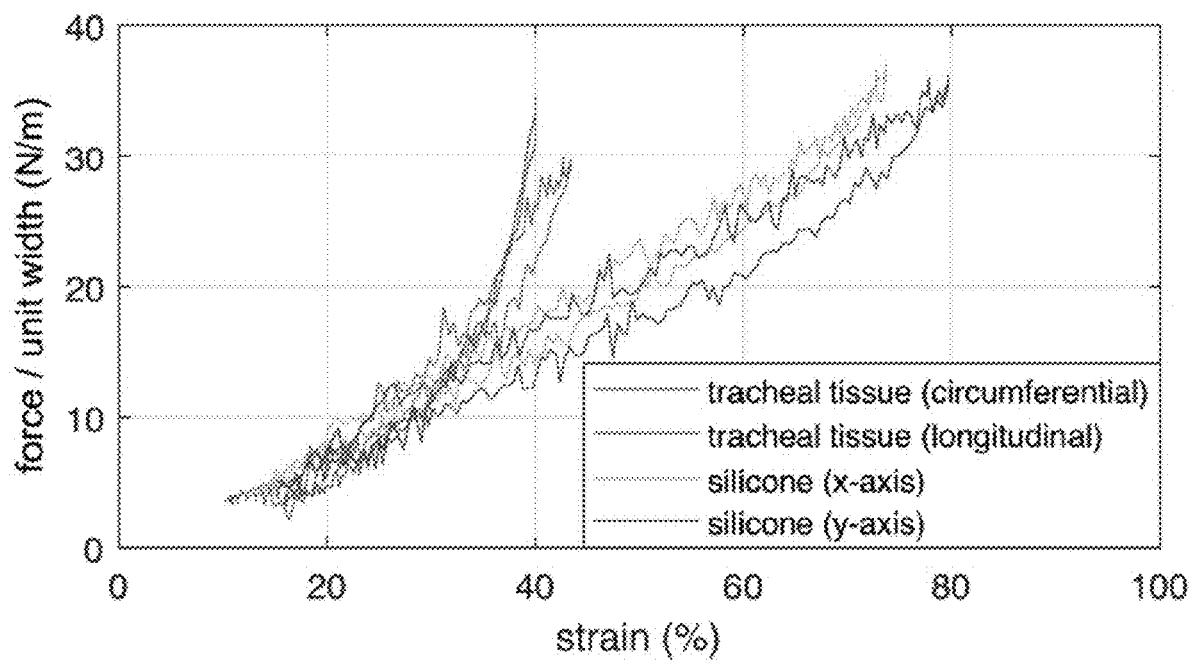
FIG. 16 is a graph illustrating force-per-unit-width over strain for tracheal tissue and a model of tracheal tissue.

A phantom trachea model was developed owing to the difficulty of creating a consistent ex vivo tracheobronchomalacia model in which the cartilage is removed while leaving the remaining tracheal tissue intact. To approximate actual tracheal tissue properties, samples of fresh porcine tissue from the membranous portion of the trachea (from the gaps between the cartilage rings) were collected. The tissue stiffness on a biaxial tester was measured. A silicone phantom was iteratively derived to match the initial tissue stiffness. FIG. 16 illustrates the force per unit width versus strain curves for the membranous porcine tracheal tissue and the phantom silicone. In FIG. 16, the x and y axes refer to arbitrary orthogonal directions on the planar silicon sample. The resulting tracheal phantom was 0.26 mm thick (True-Skin 10, Quantum Silicones). Silicone exhibits a large linear stress-strain region compared to the stiffening characteristic of tracheal tissue. Consequently, area reduction of the silicone trachea model will overestimate that of tissue.

Figure 17:
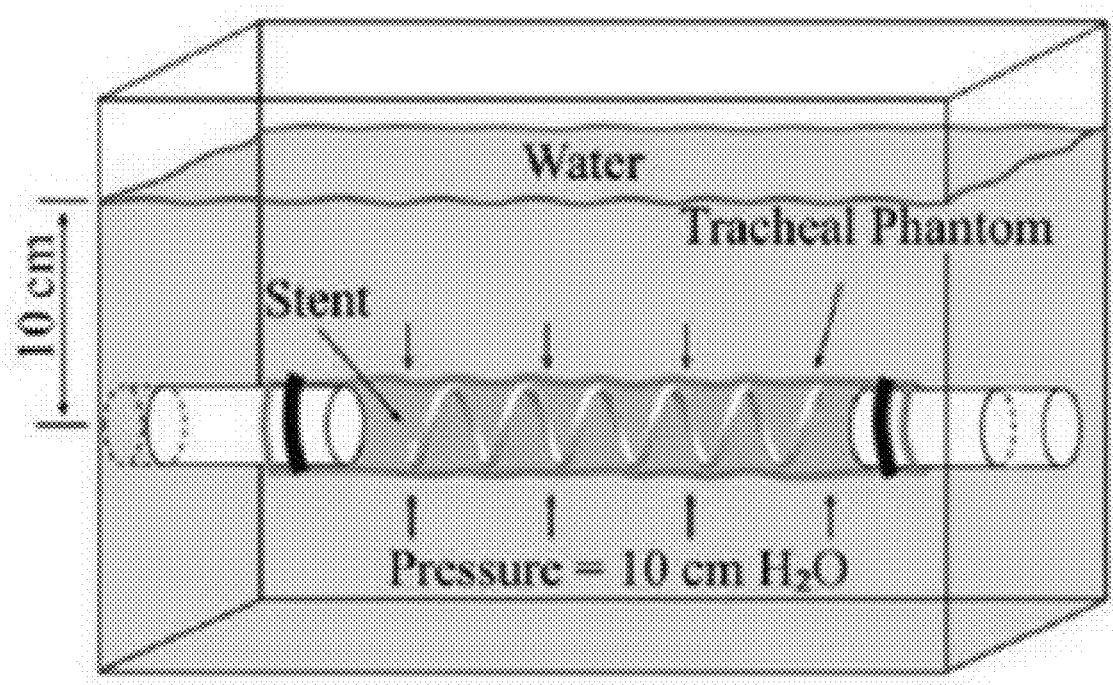
FIG. 17 is a schematic diagram of a test setup for a stent.

The phantom trachea was mounted on two co-axial rigid plastic tubes that extended through the walls of a test tank as schematically shown in FIG. 17. The two tubes enabled access to the inside of the phantom from both ends. Mineral oil was distributed on the inner surface of the phantom to reduce friction between the silicone trachea and the stent and so mimic the slippery endothelial surface of the trachea. To deliver a stent into the phantom, sutures were tied to each end of the stent so that it could be stretched and so reduced to a diameter less than that of the phantom trachea. One suture was then passed through the phantom and the stent was then positioned in the middle of the phantom. The phantom was then pressurized to increase its diameter and so allow the stent to assume a relaxed configuration. After removing the pressure, the tank was then filled with deionized water to a depth of 10 cm from the central axis of the phantom trachea.

To measure the tracheal phantom cross sectional area, red marks were created every 1 cm along the length with intermittent blue marks spaced 2.5 mm apart on the circumferential curves lines. By inserting a telescope (Karl Storz 10328AA) inside the artificial trachea, the cross section was measured as the area inside a red curve using the blue marks to calculate distance at the image depth of any given red curve. The camera calibration toolbox for Matlab was used to estimate camera parameters and to correct for image distortion. Calibration using closed curves of known area was performed yielding mean and maximum errors of 0.9% and 2.6%, respectively.

To measure the reduction in stent diameter and cross sectional area as modeled in Section II, images were taken from the top of the tank using a camera (Canon EOS 6D Mark II) with a macro lens (Canon EF 100 mm). A 5 mm pitch checkered pattern was imaged and Matlab's camera calibration toolbox was utilized to estimate the camera parameters for correcting image distortion due to refraction through water. Calibration yielded a maximum error of 0.9 pixels or 0.04 mm at 51 pixels/mm. Using the calibrated images, lines were fit to the outer edges of the two central coils and the minimum distance between the coil edges and the opposing line was taken as the reduced stent diameter.

Figure 18:
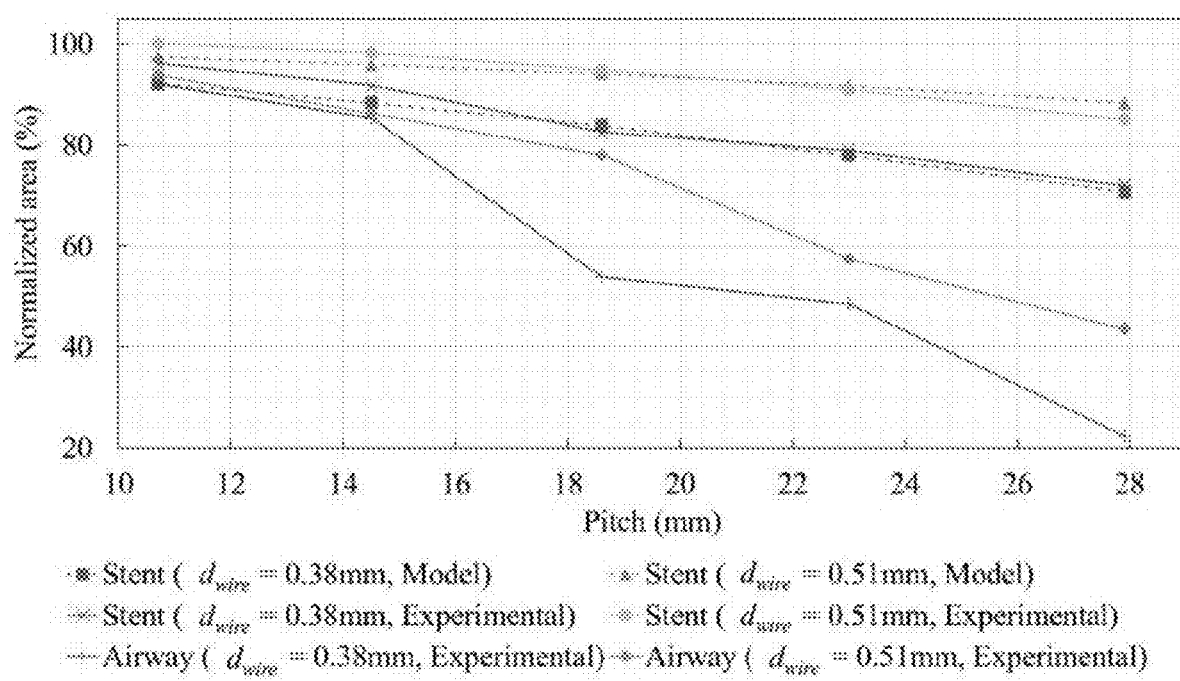
FIG. 18 is a graph of stent and phantom trachea area reduction over stent pitch for two wire diameters.

A comparison of experimentally-measured and model-predicted cross-sectional areas is plotted in FIG. 18 as a function of stent pitch. FIG. 18 illustrates stent and phantom trachea area reduction versus stent pitch for two wire diameters. The dashed curves in FIG. 18 show area reduction predicted by the model discussed in Example 1. The areas are normalized with respect to the unpressurized cross-sectional area. The effect of external pressure on the stent is to cause it to lengthen and reduce in diameter and cross-sectional area. The model closely predicts the experimentally observed reduction in stent cross sectional area (<5%).

While stent cross-sectional area decreases with increasing stent pitch, the major effect of increasing pitch is the reduction in cross section associated with tracheal phantom stretching between the coils (as illustrated in FIG. 13B). These results suggest that a stent pitch of 14.5 mm will reduce tracheal cross section area by 15% for either wire diameter. Since a real malacic airway will have more support than the phantom employed here, larger pitches can likely be employed.

Example 3: Uses of Stent Delivery and Removal Tools

To enable atraumatic stent delivery and removal, bronchoscope-guided instruments were developed. The stent delivery system includes three concentric cannulas. The stent is preloaded into the delivery system and subsequently deployed. The cannulas are sized such that a flexible bronchoscope (Karl Storz 10328AA) fits inside the lumen of the innermost cannula enabling image-based positioning in the trachea. As described herein, FIGS. 5A-5G illustrate an example of a stent delivery instrument and using the stent delivery instrument to deliver a stent.

To achieve atraumatic stent removal even when the stent has been endothelial zed, the removal system was designed to retract the stent using an unscrewing motion matching the helical pitch of the stent. The system included optical forceps (through which a bronchoscope can be inserted) that fit inside an outer cannula. The two components were connected at their proximal ends by a helical joint matching the pitch of the stent. As described herein, FIGS. 6A-6C illustrate an example of a stent removal instrument and using the stent removal instrument to remove a stent from an airway.

For stent removal, the forceps were first used to grasp the ball on the proximal end of the stent. Holding the outer cannula fixed in place, the forceps handle was then rotated. The helical joint caused the inner cannula to follow a helical retraction path causing the stent to be retracted in a follow-the-leader fashion into the outer cannula.

During retraction into the outer cannula, the stent ball would occasionally slip out of the optical forceps. Since the stent ball was then pressed against the inside of the outer cannula, it was difficult to regrasp with the forceps. For these situations, a regrasping device was used. The device included a notched outer cannula and cylindrical inner cannula. The notched outer cannula functions like a spatula. Under bronchoscopic guidance, the notched cannula was extended such that the ball enters the notch. The notched cannula was designed such that rotation of the notched cannula caused the ball to slide onto the interior of this cannula from where it could be positioned at the innermost corner of the notch and locked in place using the inner cannula. Once regrasped, helical stent retraction then proceeded as described above. As described herein, FIGS. 7A-7D illustrate an example of a regrasping device and using the regrasping device to regrasp a stent during removal.

Example 4: In Vivo Use of Stents and Bronchoscopic Examination

To evaluate stent safety as well as the delivery and removal tools, a 28-day in vivo experiment was conducted on a 20-kg (2-month old) Yorkshire swine. The stent was positioned approximately 2 cm proximal to the carina on the first day. It was removed on the 21st day and the animal was survived for an additional 7 days. Weekly bronchoscopy examinations and chest x-rays were performed. All procedures were approved by the Institutional Animal Care and Use Committee.

Based on the phantom study results of Example 2, a stent with a pitch of 18.6 mm and a wire diameter of 0.51 mm experiences a cross-sectional area reduced to 77% of the nominal area under a pressure of 10 cm $H_2O$. Since the tracheal phantom was completely unsupported, this value represents a worst-case area reduction. Consequently, these parameters would likely provide sufficient airway protection and so were selected for the in vivo test. The 18.6 mm pitch of the phantom studies corresponds to a helix angle of 25 degree so this helix angle together with a wire diameter of 0.51 mm were used to design stents for the in vivo experiment. Since the tracheal diameter of the pig was not known in advance, stents were prepared in five diameters (10.03, 11.62, 13.21, 14.80, and 16.38 mm) and two lengths, corresponding to two and three complete coils, respectively. At the start of the procedure, a chest x-ray was taken and the inner diameter of the trachea was estimated to vary between 11.4 mm to 13.2 mm in the desired region of stent deployment. To avoid stent migration, the stent should be preloaded against the tracheal tissue and so a diameter of 13.21 mm was selected for deployment. In addition, stent length was selected to be 3 coils so that approximately half of the trachea was stented.

Figure 19A:
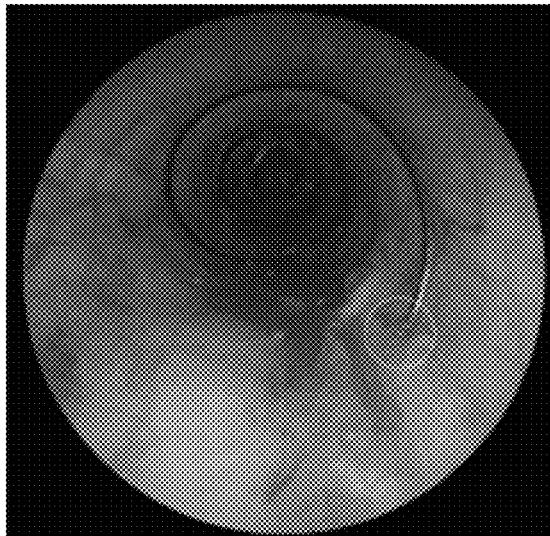
FIGS. 19A-19D illustrate bronchoscopic images of a trachea during a process of using a stent.

Stent deployment took 10 minutes and 15 seconds and the deployed stent is shown in FIG. 19A, which shows a bronchoscopic image of the trachea immediately after stent deployment. The stent was well tolerated by the animal. No coughing or other respiratory distress was observed at any time during the course of the experiment. Bronchoscopic imaging showed that, while some mucus collected on the stent wire, the tracheal tissue between the helical coils was free of mucus.

Figure 19B:
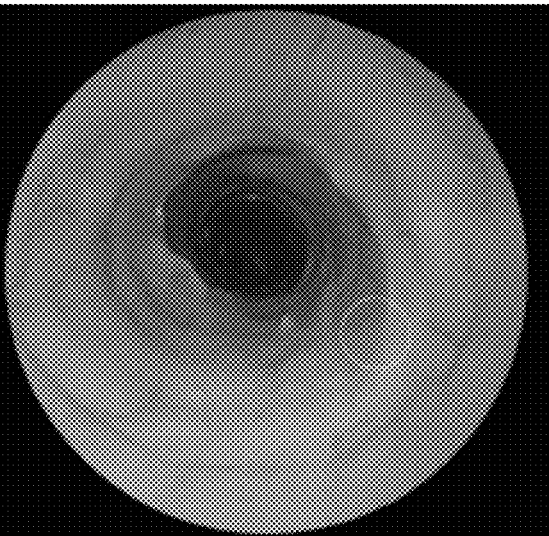
Figures 20A, 20B, 20C:
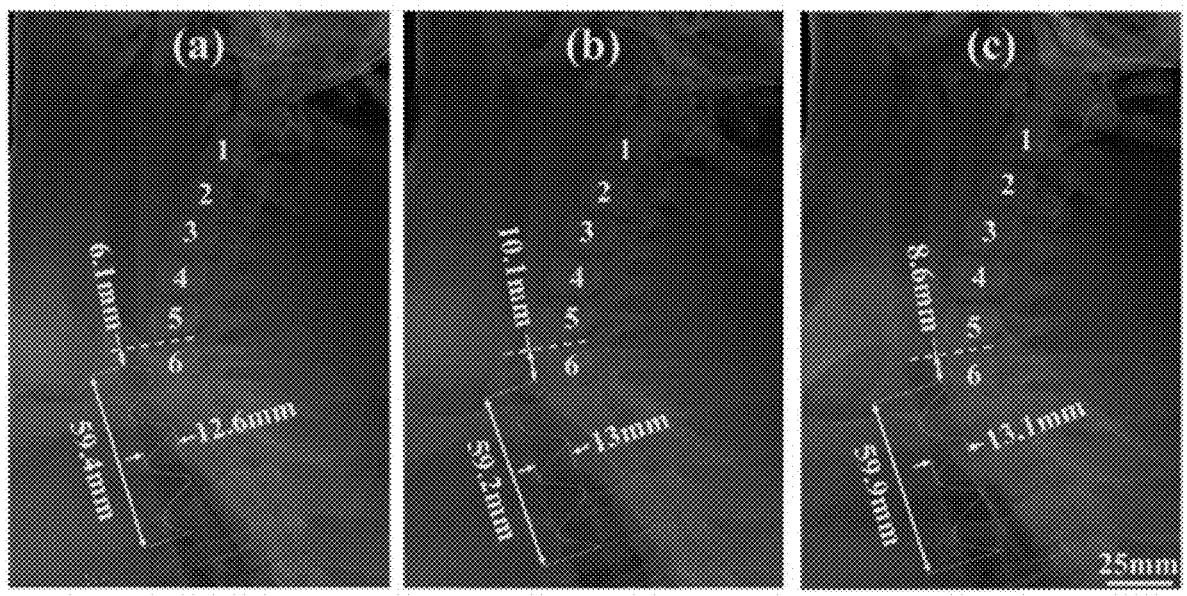
FIGS. 20A-20C illustrate lateral x-ray images of a region of a patient including a trachea during a process of using a stent.

To investigate stent migration, X-ray images were taken at the time of stent placement and then at 7, 14, and 21 days. From these images, stent length, diameter and position with respect to the vertebrae were measured. FIG. 20A-20C show lateral view x-ray images taken on the day of stent deployment, day 7 after stent deployment, and day 21 after stent deployment, respectively. Stent position along the vertebrae was observed to vary by up to 4 mm. This apparent displacement, however, may be due to differences in positioning the animal during x-ray since bronchoscopic examination showed that the stent became partially embedded in the trachea over the course of the experiment, as shown in FIG. 19B, which shows a bronchoscopic image of the trachea 21 days after stent deployment.

Stent removal took 14 minutes and 19 seconds. As shown in FIG. 19B, the ball on the proximal end of the stent was embedded in the tracheal epithelium. After suctioning the trachea to remove mucus, the removal instrument was inserted and the forceps were used to excise the ball from the tissue. Several attempts were required to securely grasp the ball. Once grasped, the stent was gently removed by "unscrewing" it from the trachea and into the outer cannula of the removal tool.

Figure 19C:
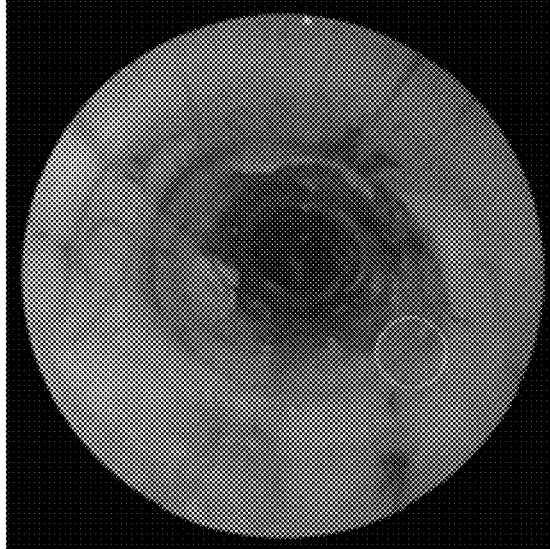
Figure 19D:
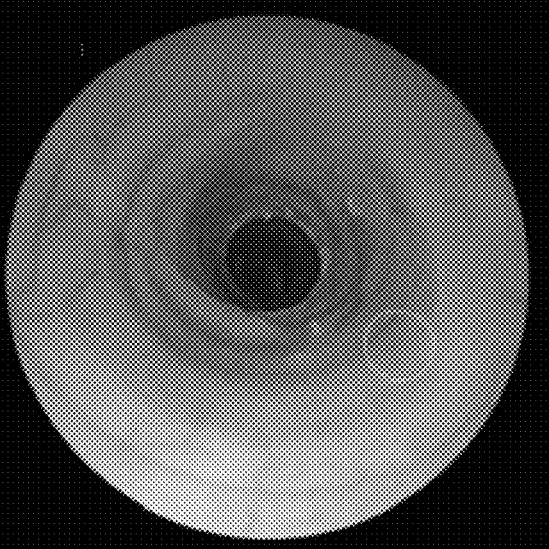

FIG. 19C shows a bronchoscopic image of the trachea just after stent removal. The location where the ball was embedded in the tissue is visible, but the tracheal epithelium is relatively undamaged. FIG. 19D shows the same region of the trachea one week after stent removal. The tissue has healed and possesses normal coloration. While a small amount of mucus is visible along portions of the helical footprint of the stent, the airway is not at all obstructed.

Example 5: In Vivo Use of Stents and Tissue Analysis

Materials

Stent and tool design and function: In this experiment, the self-expanding helical stents, as described herein, were fabricated from superelastic NiTi wire with a ball of NiTi at each tip. The wire diameter and pitch of the helix were designed to provide support comparable to a desired level of positive airway pressure, e.g., 10 cm H2O. The wire diameter was 0.51 mm and the pitch was 18.6 mm. For delivery, the stent was compressed inside a delivery cannula with its distance ball tip locked into an inner delivery cannula. Under bronchoscopic guidance (Karl Storz 10328AA), the delivery tool was navigated to the desired location in the trachea or bronchi. The outer cannula (outer diameter=6.5 mm) was slowly retracted to release the stent. The distal end of the stent was then released and the tool was retracted.

Methods

In Vivo Experiments. Five experimental Yorkshire swine animals received stents. Two additional animals that did not undergo any tracheal procedures were also used as controls. Four-week experiments were performed with the stent placed on day 0 and removed on day 21. Bronchoscopy and x-ray imaging were performed every week. For the weekly procedures, each animal was induced with a regimen of telazol 4.5 mg/kg, xylazine 2 mg/kg, and atropine 0.04 mg/kg. The animal was maintained with propofol IV 3-5 mg/kg/hr.

FIGS. 21A-21D show x-ray images that were used for tracheal size estimation and stent migration measurement in swine trachea. FIGS. 21A-21B show representative left lateral thoracic x-ray images for estimation of tracheal size. FIGS. 21C-21D show representative left lateral thoracic x-ray images for monitoring stent migration. FIG. 21A shows an x-ray image on day 0 before the stent was delivered at the desired location of stent implantation in the trachea lying near the 4th and 8th vertebrae (dotted rectangle). FIG. 21B shows a magnified view of the desired stent delivery location. As shown in FIG. 21B, the trachea diameter was estimated using the x-ray images at 3 sections (proximal to distal): d1=11.7 mm, d2=12.7 mm and d3=14.5 mm. The estimated average diameter was 13 mm. FIG. 21C shows an x-ray image after delivery of a helical stent (OD=14.7 mm, NC=3) on day 0. (D) The stent remained in its implanted position between the 4th and 8th vertebrae on day 21. The scale bars in FIGS. 21A-21D represent 20 mm. D represents the dorsal direction. V represents the ventral direction. d1-d3 represent tracheal diameters measured from the x-ray images.

For stent placement, tracheal size (diameter and length) were estimated from a left lateral thoracic x-ray image of the animal (FIGS. 21A-21B). The desired location of stent delivery was identified (FIG. 21A) and its inner diameter was measured at multiple sections in the x-ray image (FIG. 21B). It was desired to elastically preload the stent against the tracheal wall so as to prevent migration along the trachea while also avoiding migration through the tracheal wall. Because the tracheal wall thickness was measured to be greater than 1 mm, stent diameter was selected to be 2 mm larger than the estimated average airway diameter. In this way, elastic preloading against the tracheal wall would go to zero prior to penetration. Bronchoscopic examination of the airway was performed followed by stent placement. The animal was given a course of cephalexin (20 mg/kg) during recovery after stent implantation and banamine (1-2 mg/kg) to treat any inflammation as needed. Animal mentation was observed for 1-2 days for signs of any respiratory distress.

To monitor mucus clearance, Teflon discs (1 mm dia×0.1 mm thickness) were dispensed uniformly in the stented region of the trachea, and distally to it, under brochoscopic guidance. Bronchoscopic examination was performed the following week to determine if the discs had been cleared from the airway. In addition, x-ray images were taken immediately after stent placement and then weekly to assess stent position and migration in the trachea.

At the end of 4 weeks, the animals were sacrificed and the tracheas harvested (5 experimental and 2 control). The tracheas were divided into two lateral halves using dorsal to ventral cuts. The left half was used for tissue staining the right half was used for scanning electron microscopy.

Pathology. The tracheal tissue was fixed in 10% formaldehyde solution for 72 hours then washed in phosphate buffered saline (PBS) and stored in 70% Ethyl alcohol (EtOH). It was then cut longitudinally into rectangular sections (~7 mm×50 mm), which spanned adjacent stented and unstented regions. Similar tissue sections were prepared from the control animals. The fixed tissue was then embedded in paraffin, and histologic slides were prepared by cutting 4 μm sections and staining with hematoxylin and eosin (H&E). The stained tissue on each slide was then demarcated into 7 mm subsections and classified as follows:

1. Stented region with wire contact (SWC): Subsection includes tissue lying directly under wire of helical stent,
2. Stented region with no wire contact (SNC): Subsection located within stented region, but not touching stent wire,
3. Unstented (UT): Subsection outside of stented region, and
4. Control (CL): Subsection from an unstented animal.

The slides were randomized and then reviewed by a pathologist (VYJ) blinded to the animal group and subsection classification. The subsections on each slide were semi-quantitatively assessed and graded for fibrosis, inflammation, granulation tissue, foreign body response, and tissue damage and extent (involving surface epithelium, submucosa, and cartilage). Each variable was graded using a four-tier scale: absent, low, medium and high. Absent and low grades for each variable were considered within normal physiological spectrum.

Scanning electron microscopy. Tissue samples were fixed in 4% methanol free paraformaldehyde solution (Polysciences Inc., Warrington, Pa.) for 24 hours. The tissue was then washed with PBS and dehydrated by submerging it in increasing concentration of EtOH solutions (25%, 50%, 75% and 95% EtOH by volume) for 2 hours in each solution. Rectangular tissue sections including regions in contact with the stent wire were cut and submerged in hexamethyldisilazane (Polysciences Inc., Warrington, Pa.) for 10 min. The tissue was then desiccated by vacuum drying. The desiccated tissue was mounted on a 12 mm diameter metal stub and sputter coated with 5 nm of platinum/palladium 80/20 alloy (EMS 150T S Metal Sputter Coater). Scanning electron microscopy (Zeiss EVO 55 Environmental SEM) was performed across the stented region. Images were captured in sequence and stitched together extending across the width of the stent wire contact region. The width of the unciliated region in each tissue was measured and used for estimating the percentage of unciliated area per unit stented area.

Results

In vivo experiment outcomes and recovery. Stents were successfully implanted and removed in the 5 animals without complications. Each animal was implanted with a single stent for the study duration. The animals did not exhibit any symptoms or respiratory distress associated with the stents. Results are summarized in Table 1 below.

| Animal # | Stent size: (Outer diameter, number of coils) | Stent migration | Stent deployment time (minutes) | Stent removal time (minutes) | Unciliated region width (μm) | Unciliated area per unit stented area (%) |
|---|---|---|---|---|---|---|
| 1 | 12.7 mm, 3 | No | 2.58 | 10.25 | Coil #1: 812<br>Coil #3: 520 | 4.1 |
| 2 | 4.3 mm, 3 | No | 6.98 | 1.88 | Coil #1: 869<br>Coil #2: 676<br>Coil #3: 652 | 4.4 |
| 3 | 14.3 mm, 3 | No | 2.32 | 2.65 | Coil #1: 843<br>Coil #2: 595<br>Coil #3: 848 | 4.5 |
| 4 | 12.7 mm, 2 | No | 8.45 | 1.62 | Coil #1: 1965 | 12.1 |
| 5 | 11.1 mm, 3 | Yes | 5.02 | 1.85 | | |

Procedures: Stent delivery and removal were straightforward. Delivery time averaged 5.07±2.69 min and removal time was 3.65±3.70 min. FIGS. 22A-22D show endoscopic images of the swine trachea. FIG. 22A shows an endoscopic image of the swine trachea immediately after the stent was delivered. FIG. 22B shows an endoscopic image of the swine trachea one week after the stent was delivered. FIG. 22C shows an endoscopic image of the swine trachea three weeks after the stent was delivered, immediately after stent removal. FIG. 22D shows an endoscopic image of the swine trachea four weeks after the stent was delivered, one week after stent removal. FIGS. 22E-22H show endoscopic images during airway mucus flow assessment by clearance of dispensed Teflon discs. FIG. 22E shows an endoscopic image of the swine trachea with Teflon discs distributed on the trachea in the stented region just after stent delivery. FIG. 22F shows an endoscopic image of the swine trachea one week later when Teflon discs have been cleared despite presence of stent. FIG. 22G shows an endoscopic image of the swine trachea with Teflon disks dispensed on trachea three weeks after the stent was delivered, immediately after stent removal. FIG. 22H shows an endoscopic image of the swine trachea after the Teflon disks have been cleared one week after removal, indicating removal did not affect mucus clearance.

Tracheal irritation was minor during stent delivery (FIG. 22A) and removal (FIG. 22B). In 3 animals, portions of the stent had become endothelialized and in 4 animals the proximal ball end which needed to be grasped for removal was endothelialized. In the latter cases, the forceps of the removal tool were successfully used to grasp the ball through the endothelium. In all cases, the corkscrew motion of the tool for retracting the stent into the cannula was successful in minimizing tracheal abrasion during removal (FIG. 22C).

Stent migration: Stent position in the weekly X-ray images was compared with the position measured immediately after placement (FIGS. 21C-21D). Stent position measured with respect to the vertebrae was noted to vary up to 4 mm. This variation is probably due to the difference in positioning of the animal during X-ray. To the resolution of our measurements, the stents did not migrate in 4 out of 5 animals throughout the 3-week stenting period (FIGS. 21C-21D). While stent migration was observed in 1 animal (#5) due to underestimation of tracheal diameter, the stent remained within the trachea and the animal did not exhibit any signs of respiratory distress throughout the 3-week stenting period.

Mucus clearance: Mucus flow was maintained throughout the stenting period as well as after stent removal. The Teflon discs dispensed over, and distal to, the stented section of tracheal wall each week were cleared and absent during the following week's bronchoscopic examination (FIGS. 21E-21F and 21G-21H). Short-term mucus flow was also captured by recording video for 20 minutes after disc dispensing. Flow on the lateral walls is directed at roughly 45 degrees from the dorsal to ventral surfaces.

Pathology review: Eleven longitudinal tracheal tissue sections were collected from the 4 experimental animals that did not experience stent migration (animals #1-4). Four tracheal tissue sections were also collected from 2 control animals. The stained slides were divided into a total of 69 subsections of 7 mm width with 11, 25, 17 and 16 subsections categorized, respectively, as stented region with wire contact (SWC), stented region with no wire contact (SNC), unstented (UT), and control (CL). Tissue was assessed with respect to inflammation, granulation tissue, fibrosis, and tissue damage and extent. Representative microscopic images of all the tissue groups are presented in FIGS. 23A-23G. The results of the blinded review are summarized in FIGS. 24A-24L.

FIGS. 23A-23G show Hematoxylin and Eosin (H&E) stained lateral tracheal sections from a stented (FIGS. 23B-23F) and a control (CL) animal (FIG. 23G). FIG. 23A show tracheal sections divided into 7 mm wide subsections. Stent wire contact regions (SWC) are positioned in center of subsections 2 and 4. Regions 1, 3 and 5 are in between or adjacent to the stent wire and were thus classified as stented with no wire contact (SWCSNC). FIGS. 23B-23E show images at magnification 5× (left image of each of FIGS. 23B-23E, scale bar: 200 μm) and 20× (right image of each of FIGS. 23B-23E, scale bar: 100 μm) in SWC (FIGS. 23C and 23E) and stented with no wire contact (SNC) (FIGS. 23B and 23D) subsections. Inflammation and granulation levels were high in stented subsection 2 (FIG. 23C) and medium in stented subsection 4 (FIG. 23E). The high level of inflammation in FIG. 23C (right image) shows densely confluent cellular areas primarily composed of numerous lymphocytes and macrophages. The medium level of inflammation in FIG. 23E (right image) shows infiltration of lymphocytes and macrophages, occasionally clustered in groups. SNC subsection 1 (shown in FIG. 23B), subsection 3 (shown in FIG. 23D), and subsection 5 (not shown) had low inflammation and no granulation or fibrosis, comparable to an unstented (UT) tissue sample from the same animal (shown in FIG. 23F) and from a control animal (CL) (shown in FIG. 23G).

FIG. 23A shows a representative slide of stented animal that included 2 coils of the stent (tissue subsections 2 and 4). The foreign body response components are significantly higher in these SWC subsections, which includes inflammation (FIG. 23C) and tissue fibrosis (FIG. 23E). The adjoining SNC tissue subsections on the other hand show low levels of foreign body response comparable to those in UT regions (FIG. 23F) and even CL animals (FIG. 23G).

FIGS. 24A-24L summarizes the histological evaluation of tissues collected from all the experimental and control animals. FIGS. 24A-24L show normalized comparisons of stented and control tissue in terms of inflammation, granulation, fibrosis and tissue damage. Tissue sub-sections (sample size, n=69) were semi-quantitatively assessed and graded by pathologist blinded to tissue classification (CL, UT, SNC and SWC) on the presence of eosinophils (FIG. 24A), neutrophils (FIG. 24B), macrophages (FIG. 24C), mast cells (FIG. 24D), lymphocytes (FIG. 24E), overall inflammation (FIG. 24F), granulation tissue (FIG. 24G), fibrosis (FIG. 24H), and tissue damage in the epithelium (FIG. 24I), submucosa (FIG. 24J), and cartilage (FIG. 24K). A 4-tier scale was used for grading: absent/no damage (dark green bars), low/mild (light green bars), medium/moderate (yellow bars) or high/severe (red bars). Each bar represents the percentage of tissue sub-sections in each grade normalized to the total number of tissue sub-sections in the respective tissue group (sample sizes, n=16, 17, 25 and 11 for CL, UT, SNC and SWC, respectively).

With respect to inflammation, granulation tissue formation, and fibrosis, these secondary effects of the stent were highly localized within the subsections in which the stent wire was in direct contact with the tissue. Those sections without wire contact (SNC and UT) were comparable to those from the control animals (CL subsections). Only for tissue damage did the effect of the stent extend into the SNC subsections, and this damage was graded as mild. Mild inflammation (comprised of mostly lymphocytes) was observed in SNC and UT subsections, but this was judged to be within the spectrum of normal physiologic response.

The SWC subsections showed macrophage levels to be high in 18% and medium in 36% of the tissue subsections (FIG. 24C) indicative of foreign body clean up and injury repair. Components of acute inflammation (eosinophils (FIG. 24A) and neutrophils (FIG. 24B)) were low or absent in >80% of the SWC subsections as expected since the stent had been removed 1 week prior to tissue harvest. There was no foreign body giant cell reaction in any of the tissue subsections indicating absence of granulomatous inflammation associated with infection, autoimmune, toxic, allergic, drug, and neoplastic conditions. Formation of granulation tissue (FIG. 24G) was observed to be high in 9% and medium in 45% of the SWC subsections. About 40% of the SWC tissue subsections exhibited medium level of fibrosis (FIG. 24H) present in the subepithelial layer. There was evidence of tissue damage in response to direct contact with the stent in SWC subsections. About 25% of the SWC tissue subsections had severe to moderate damage in the epithelial layer (FIGS. 24I-24J).

Distribution of cilia. SEM imaging was used to determine over what region the stent impacted the distribution of cilia on the epithelium in the 4 animals in which the stent did not migrate. Matching the results of the mucus clearance testing, it was observed that the cilia were present everywhere in the stented regions except in the neighborhood where the stent wire contacted the tissue (FIGS. 25A-25D). FIGS. 25A-25D shows Scanning Electron Microscope (SEM) images of ciliated regions. FIG. 25A shows a composite image crossing stent wire contact region. The wire was oriented vertically with contact roughly centered in the unciliated region (between black dotted lines). FIG. 25B shows a magnified view of border between with the ciliated (left of dotted line) and the unciliated (right of dotted line) epithelium. FIG. 25C shows a magnified view of the unciliated region. FIG. 25D shows a magnified view of the ciliated region. Scale bars represent 20 µm.

The width of the non-ciliated region averaged over 9 tracheal tissue samples was 874±402 µm, which is less than twice the wire diameter of 510 µm. This result also tends to confirm our X-ray observations that the stents did not migrate in these 4 animals. The unciliated area per unit stented area in the 4 animals ranged from 4.1 to 12.1% (Table 1 above). In ideal conditions, only the area below the stent wire (width=wire diameter) would be unciliated, the area effected would be 3 to 3.3% of stented area.

Discussion

These experiments confirmed the benefits of a helical stent design. When properly sized, the screw-like shape of the stent resisted migration as evidenced by the x-ray and SEM studies. Estimation of tracheal diameter for stent selection was important since an undersized stent could migrate along the trachea while an oversized stent could migrate through the tracheal wall. With tracheal wall thicknesses in the animal model in the range of 1.2-2.2 mm, the stent diameters were selected to be 2 mm larger than the inner tracheal diameter as measured by x-ray. This value was sufficient to prevent migration while also avoiding tracheal penetration.

In addition, the foreign body response and tissue damage was localized to the region of stent wire contact (~4-12%) leaving most (~88-96%) of the stented region (which were between the wire loops) unaffected. This enabled mucus to flow through the stented region with the wire perhaps acting only as a speedbump, but not stopping the flow as in the case of silicone or covered metallic stents where foreign body contact would be close to 100%. Mucus clearance was maintained throughout the stenting period as well as after removal and the animals did not require suctioning or any other form of assistance.

An additional benefit of the helical design determined from these experiments was the ability to remove the stent, even when endothelialized, by using an unscrewing motion matching the pitch of the helix. This substantially reduces the trauma compared to the removal of a standard mesh stent. The pathologic features and SEM images both confirm that tissue damage, arising both from having the stent in place and from removing it, are localized to the contact regions with the stent wire. Pathologic assessment of response to placement of the stent showed that inflammation, granulation tissue formation, and fibrosis were confined to the area of the trachea that were in direct contact with the stent (SWC). Since the fibrosis was subepithelial, it had no effect on the ciliated mucosal function. Furthermore, the SWC sections were the primary areas showing tissue damage secondary to the foreign body, evidenced by increased moderate-to-severe tissue damage. This damage was primarily observed in the superficial epithelial layers, and only mild tissue damage was seen in adjacent SNC subsections. These findings, in conjunction with observations of only localized loss of cilia in the areas of direct stent contact and maintained mucus flow, indicate that tissue reaction and tissue damage are localized to areas of direct contact with the stent, and neighboring tracheal regions are only minimally affected.

While the SWC sections showed increased inflammation, granulation tissue, and fibrosis, these changes were largely absent in SNC sections. The primary component of the inflammatory response was lymphocytes and macrophages; foreign body giant cell response was not a feature. The findings in SWC and SNC one-week post-stent removal were features of tissue repair and damage resolution (granulation tissue) with no to low level of active damage (i.e. low acute inflammation components in FIGS. 24A-24B). Furthermore, there were areas of intact mucosa overlying the SWC and SNC areas indicating tissue regeneration. Overall these indicate that the tissue damage was not permanent and overall function was restored.

This study demonstrated how a helical self-expanding stent could overcome the challenges of existing stent designs. Its screw-like geometry provided radial support to the airway while resisting migration, minimally impeding mucus flow and enabling easy removal using an unscrewing motion.

Example 6: Use of Molded Stents in Models of Tracheal Airway

Figure 26A:
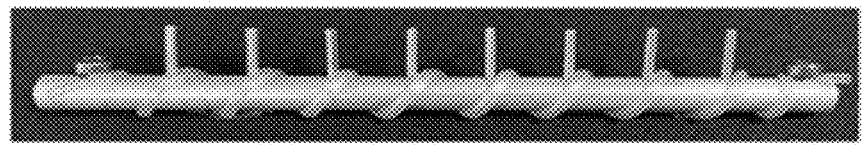
FIGS. 26A-26C illustrate a process used to form a stent containing light-curable material.
Figure 26B:
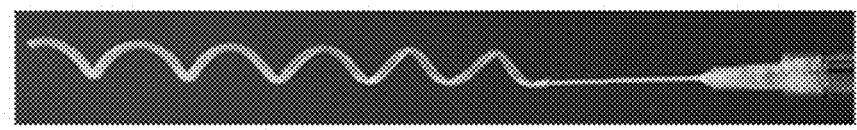
Figure 26C:
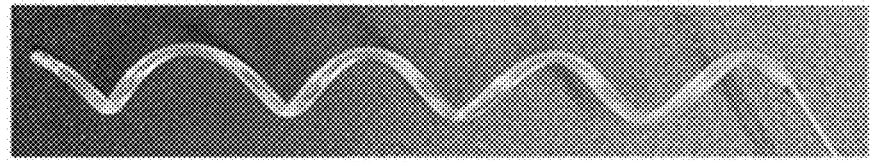

In this example, a stent containing curable material was produced and then used on a model of an airway. FIGS. 26A-26C illustrate formation of the stent containing curable material. First, as shown in FIG. 26A, a polymer tubing was used as the outer shell of the stent. The polymer tube was wrapped around a cylindrical member to form a helical arrangement. To set the shape of the polymer tube into the helical arrangement, heat was applied to the polymer tube. Next, as shown in FIG. 26B, a curable material was injected into the polymer tube using a syringe. Finally, as shown in FIG. 26C, radiopaque metal screws were inserted into the open ends of the polymer tube.

Figure 27A:
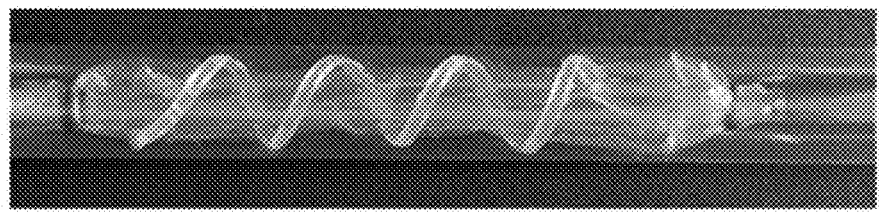
FIGS. 27A-27E illustrate a process used to insert a stent containing light-curable material in a tubular model of an airway.
Figure 27B:
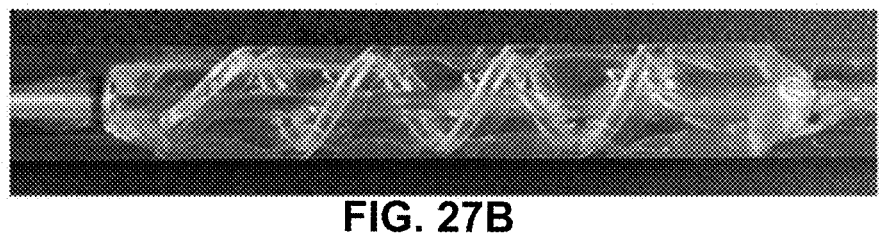
Figure 27C:
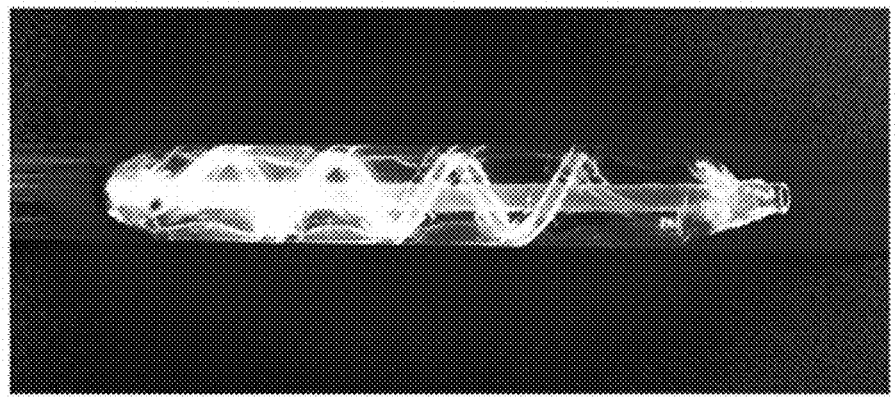
Figure 27D:
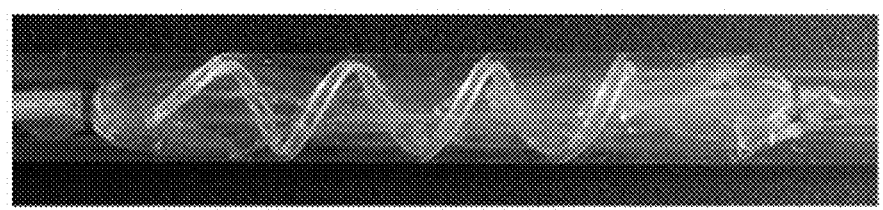
Figure 27E:
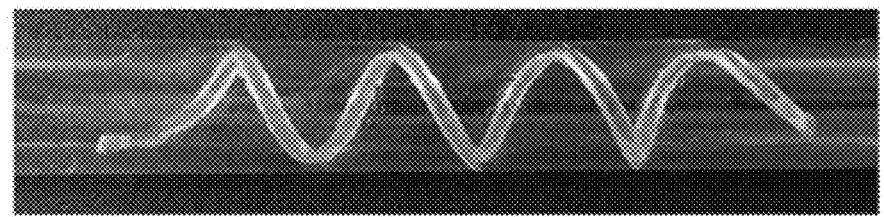

FIGS. 27A-27E illustrate use of the stent in a tube with uniform diameter. The stent was wrapped around a deflated balloon catheter. Then, as shown in FIG. 27A, the balloon catheter with the stent was placed at a desired location within the tube. Next, as shown in FIG. 27B, the balloon catheter was inflated to stretch the tube by about 2 millimeters in diameter. After the balloon catheter was inflated, as shown in FIG. 27C, the stent was exposed to UV light to cure the curable material within the stent. Then, as shown in FIG. 27D, the balloon was deflated. Finally, as shown in FIG. 27E, the balloon catheter was retracted and removed from the tube, leaving the stent in place within the tube.

Figure 28A:
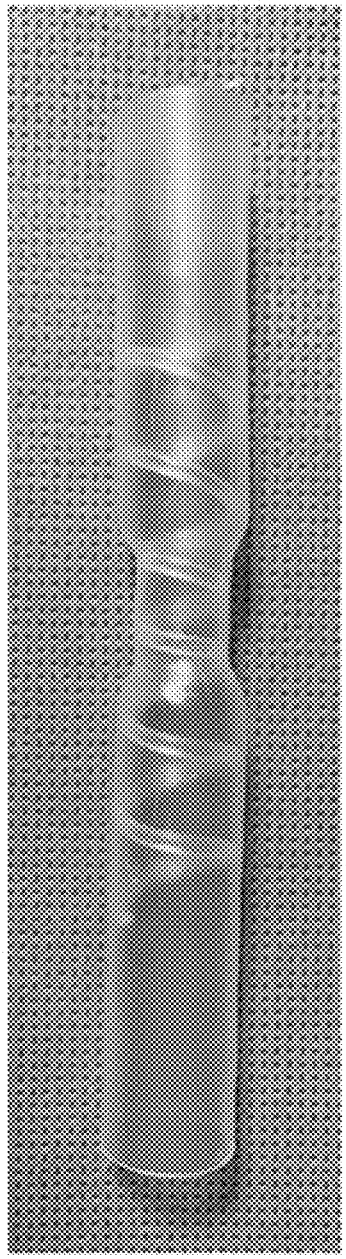
FIGS. 28A-28B illustrate an example of a stent used in a tubular model of an airway having a non-uniform diameter.
Figure 28B:
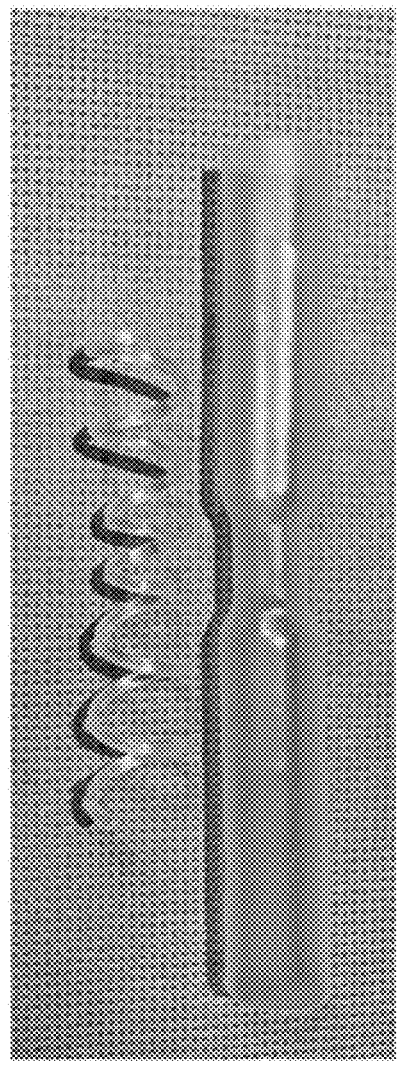

The molded stents can also be made to provide a custom fit to an airway with variations in diameter. When a stent is inserted over a balloon in an airway of varying cross section and the balloon is inflated, the balloon cross section and that of the stent conform to the varying dimensions of the airway cross section. Once cured, the stent maintains this conforming airway shape along its length. Using this approach, as shown in FIG. 28A, a stent was inserted and cured inside a tube with a significant reduction in diameter over a length of about 1 centimeter toward the center of the stent. FIG. 28B shows the stent after it was removed from the tube. As shown in FIG. 28B, a central portion of the stent had a reduced diameter compared to a remainder of the stent.

What is claimed is:

1. A method for removing a stent from an airway of a patient, the method including:
   inserting a removal instrument into the airway of the patient, the removal instrument including a cannula;
   engaging the removal instrument with the stent, in which engaging the removal instrument with the stent comprises grasping the stent by a grasping device of the removal instrument, the grasping device connected to the cannula of the removal instrument by a helical joint; and
   rotating a portion of the removal instrument to cause retraction of the stent into the cannula.

2. The method of claim 1, in which the removal instrument includes an imaging device used to produce imagery of the airway as the removal instrument is inserted into the airway of the patient.

3. The method of claim 1, in which engaging the removal instrument with the stent comprises:
   grasping the stent by a grasping device of the removal instrument, the grasping device connected to the cannula of the removal instrument by a helical joint.

4. The method of claim 1, further comprising:
   compressing the stent within the cannula of the removal instrument during or after the retraction of the stent into the cannula; and
   retracting the removal instrument with the compressed stent relative to the airway.

5. The method of claim 1, in which the stent comprises a helically arranged structure.

6. The method of claim 5, in which the portion of the removal instrument comprises a helical joint, and a pitch of the helical joint substantially matches a pitch of the helically arranged structure of the stent.

7. The method of claim 5, in which a helical angle of the helically arranged structure is between 15 and 35 degrees.

8. The method of claim 5, in which a pitch and a helix diameter of the helically arranged structure is configured to provide a positive pressure ventilation of the airway of the patient between 5 and 20 cm $H_2O$.

9. The method of claim 5, in which a pitch of the helically arranged structure is between 10.7 and 27.9 millimeters.

10. The method of claim 5, in which a thickness of a wire of the helically arranged structure is between 0.1 and 1 millimeters.

11. The method of claim 5, in which engaging the removal instrument with the stent comprises engaging the removal instrument with a protruding element on an end of the helically arranged structure.

12. The method of claim 11, in which the protruding element comprises a width at least 10% greater than a thickness of a wire of the helically arranged structure.

13. The method of claim 11, in which the protruding element is a first protruding element, the end of the helically arranged structure is a first end of the helically arranged structure, and the helically arranged structure comprises a second protruding element on a second end of the helically arranged structure.

14. The method of claim 11, in which the protruding element is a ball.

15. The method of claim 1, in which the cannula is a second cannula of the removal instrument, and the portion of the removal instrument corresponds to a portion of a first cannula of the removal instrument arranged in the second cannula.

16. The method of claim 1, in which engaging the removal instrument with the stent comprises operating a grasping device of the removal instrument to grasp onto a portion of the stent.

17. The method of claim 16, in which the grasping device comprises one or more movable jaws.

18. The method of claim 16, in which the grasping device is connected to the portion of the removal instrument and extends distally from a distal end of the portion of the removal instrument.

19. The method of claim 1, in which rotating the portion of the removal instrument to cause the retraction of the stent into the cannula comprises retracting the portion of the removal instrument into the cannula.

20. The method of claim 1, in which the portion of the removal instrument is threadedly engaged with the cannula.

21. A method for removing a stent from an airway of a patient, the method including:
   inserting a removal instrument into the airway of the patient, the removal instrument including a cannula;
   engaging the removal instrument with the stent, in which the stent comprises a helically arranged structure, a first protruding element on a first end of the helically arranged structure, and a second protruding element on a second end of the helically arranged structure, and in which engaging the removal instrument with the stent comprises engaging the removal instrument with the first protruding element on the first end of the helically arranged structure; and
   rotating a portion of the removal instrument to cause retraction of the stent into the cannula.

22. The method of claim 21, in which the first protruding element or the second protruding element comprises a width at least 10% greater than a thickness of a wire of the helically arranged structure.

23. The method of claim 21, in which the first protruding element or the second protruding element is a ball.

* * * * *